(12) United States Patent  
Aoki

(10) Patent No.: US 7,733,090 B2
(45) Date of Patent: Jun. 8, 2010

(54) MAGNETIC FIELD GENERATOR

(75) Inventor: Masaaki Aoki, Takatsuki (JP)

(73) Assignee: Hitachi Metals, Ltd., Tokyo (JP)

( * ) Notice: Subject to any disclaimer, the term of this patent is extended or adjusted under 35 U.S.C. 154(b) by 543 days.

(21) Appl. No.: 11/631,259

(22) PCT Filed: Jun. 28, 2005

(86) PCT No.: PCT/JP2005/011843

§ 371 (c)(1),
(2), (4) Date: Dec. 29, 2006

(87) PCT Pub. No.: WO2006/003892

PCT Pub. Date: Dec. 1, 2006

(65) Prior Publication Data

US 2008/0303522 A1  Dec. 11, 2008

(30) Foreign Application Priority Data

Jul. 1, 2004  (JP)  .............................. 2004-195878

(51) Int. Cl.
*G01V 3/00* (2006.01)
(52) U.S. Cl. .................................... 324/319
(58) Field of Classification Search ......... 324/300–322; 335/296–306
See application file for complete search history.

(56) References Cited

U.S. PATENT DOCUMENTS

| | | | | |
|---|---|---|---|---|
| 4,660,013 A | * | 4/1987 | Laskaris et al. | ............. 335/299 |
| 4,672,346 A | * | 6/1987 | Miyamoto et al. | ........... 335/296 |
| 4,848,103 A | * | 7/1989 | Pelc et al. | .................... 62/51.1 |
| 4,998,976 A | | 3/1991 | Rapoport | |
| 5,063,934 A | | 11/1991 | Rapoport et al. | |
| 5,320,103 A | | 6/1994 | Rapoport et al. | |
| 5,462,054 A | * | 10/1995 | Rapoport et al. | ............ 335/296 |
| 5,652,517 A | | 7/1997 | Maki et al. | |

(Continued)

FOREIGN PATENT DOCUMENTS

CN  1272774 A  11/2000

(Continued)

OTHER PUBLICATIONS

Office Action to the corresponding Chinese Application No. 200580022400.1 w/English translation.

(Continued)

*Primary Examiner*—Brij B Shrivastav
*Assistant Examiner*—Dixomara Vargas
(74) *Attorney, Agent, or Firm*—Kratz, Quintos & Hanson, LLP

(57) ABSTRACT

There is provided a magnetic field generator which is capable of generating a uniform magnetic field of a desired intensity easily and stably without increasing running cost. The magnetic field generator includes a pair of plate yokes. The plate yokes have opposed surfaces provided with magnetic pole respectively. The magnetic pole includes a permanent magnet group whereas the magnetic pole includes a permanent magnet group. Each of the permanent magnet groups is formed substantially in a disc like shape, as an integral body made of a plurality of permanent magnets and a plurality of heat conducting members. Tubular heaters, buried in the plate yokes, generate heat, which is conducted via the plate yokes to each permanent magnet and each heat conducting member which constitute the permanent magnet groups.

17 Claims, 29 Drawing Sheets

U.S. PATENT DOCUMENTS

| | | | |
|---|---|---|---|
| 6,297,634 B1 * | 10/2001 | Aoki | 324/315 |
| 6,332,324 B1 * | 12/2001 | Saho et al. | 62/51.1 |
| 6,844,801 B2 * | 1/2005 | Huang et al. | 335/296 |
| 6,853,855 B2 * | 2/2005 | Ideler | 600/410 |
| 7,084,633 B2 | 8/2006 | Aoki et al. | |
| 7,140,420 B2 * | 11/2006 | Arik et al. | 165/80.2 |
| 7,323,135 B2 * | 1/2008 | Choi et al. | 266/90 |
| 2002/0171526 A1 | 11/2002 | Laskaris et al. | 336/110 |
| 2003/0006771 A1 | 1/2003 | Goto et al. | |
| 2005/0092395 A1 | 5/2005 | Aoki et al. | 148/102 |

FOREIGN PATENT DOCUMENTS

| | | |
|---|---|---|
| EP | 1 004 270 A1 | 5/2000 |
| EP | 1 102 077 A2 | 5/2001 |
| JP | 63-43649 | 2/1988 |
| JP | 63-278310 | 11/1988 |
| JP | 02-016702 | 1/1990 |
| JP | 2-23010 | 5/1990 |
| JP | 2-276211 | 11/1990 |
| JP | 03210235 A * | 9/1991 |
| JP | 05-212012 | 8/1993 |
| JP | 5-212012 | 8/1993 |
| JP | 05337098 A * | 12/1993 |
| JP | 8-266506 | 10/1996 |
| JP | 2001-70280 | 3/2001 |
| JP | 2003-24296 | 1/2003 |
| JP | 2003-305021 | 10/2003 |
| JP | 2004-41715 | 2/2004 |
| JP | 2005065752 A * | 3/2005 |
| WO | WO99/65392 A1 | 12/1999 |

OTHER PUBLICATIONS

Supplementary European Search Report dated Aug. 24, 2009 for corresponding EPC Patent Application No. 05765248.9.

* cited by examiner

FIG. 3
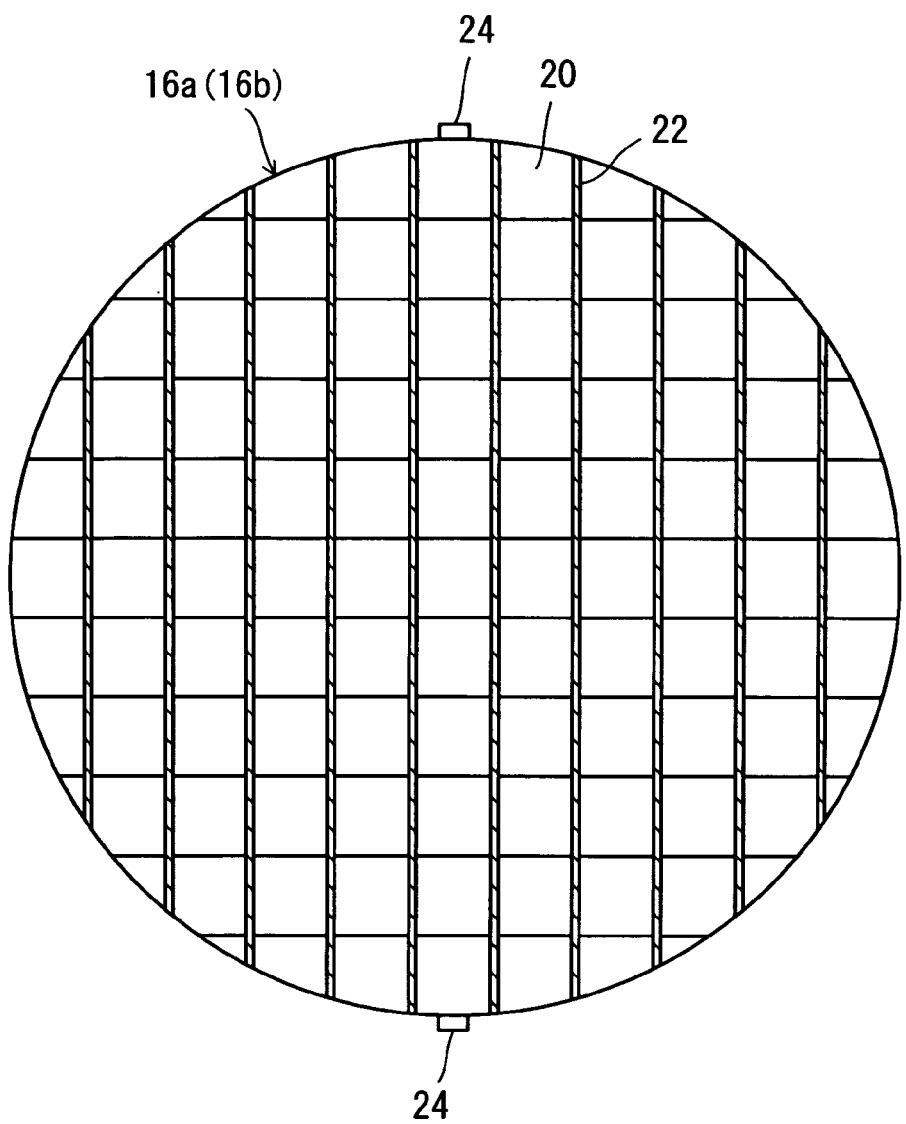
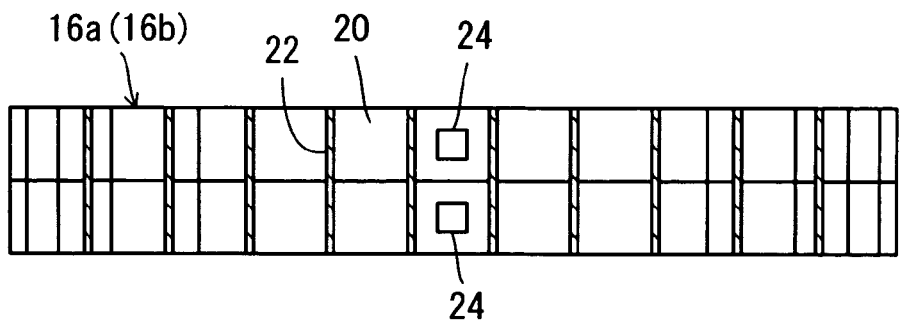

FIG. 4
(a)
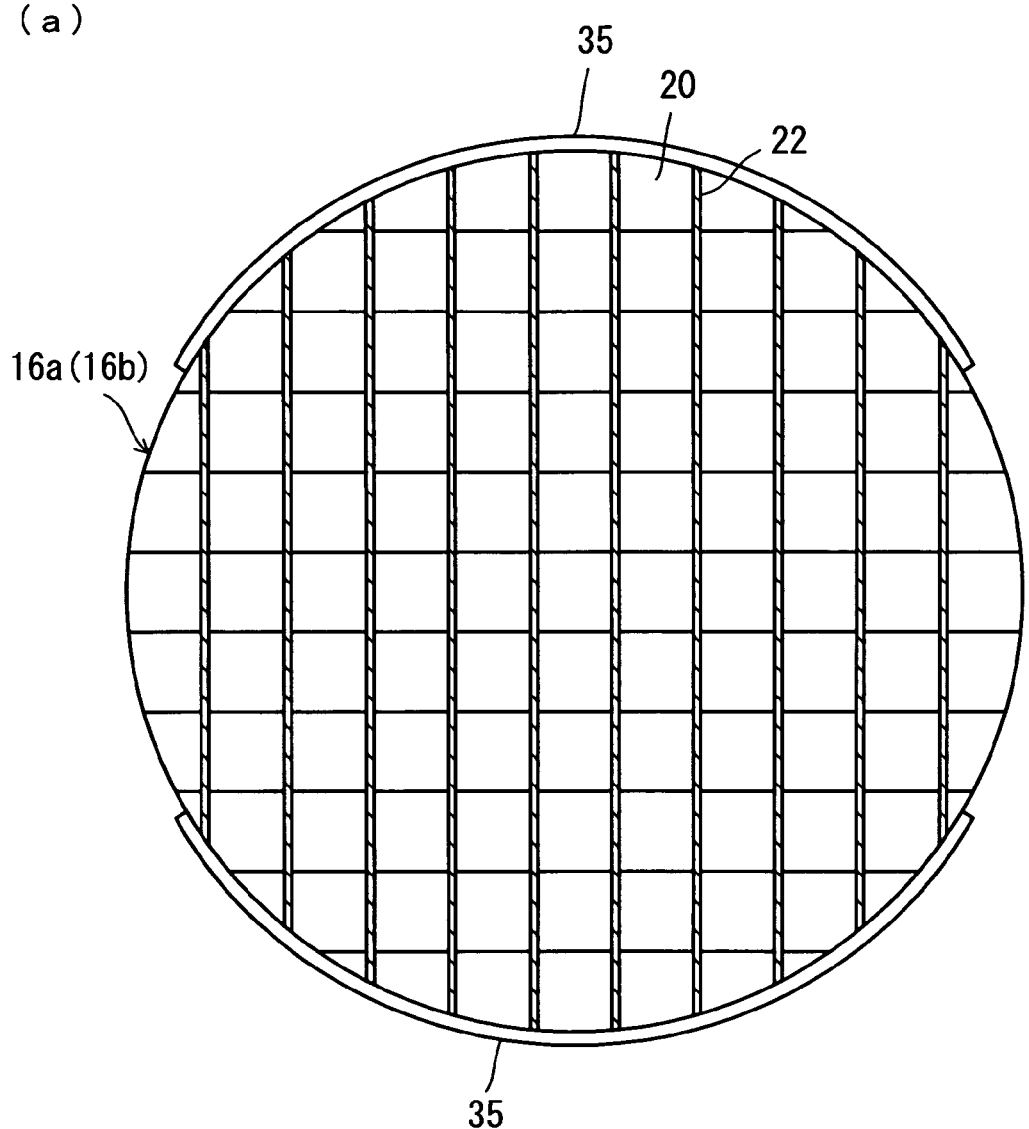
(b)
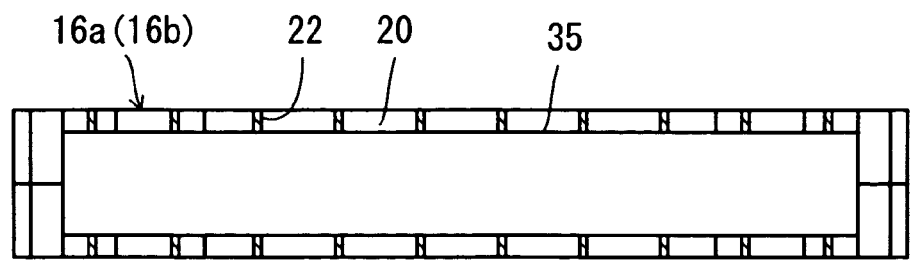

FIG. 6
(a)
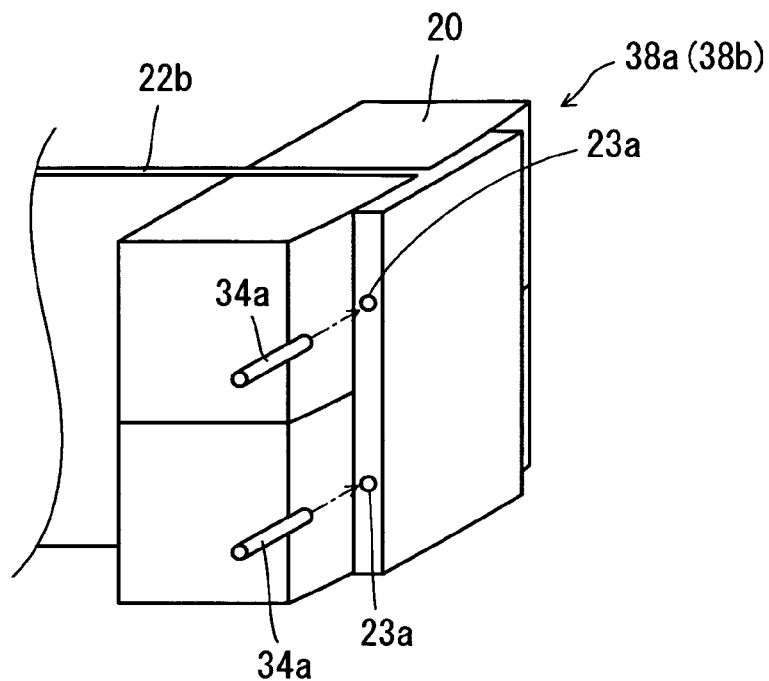
(b)
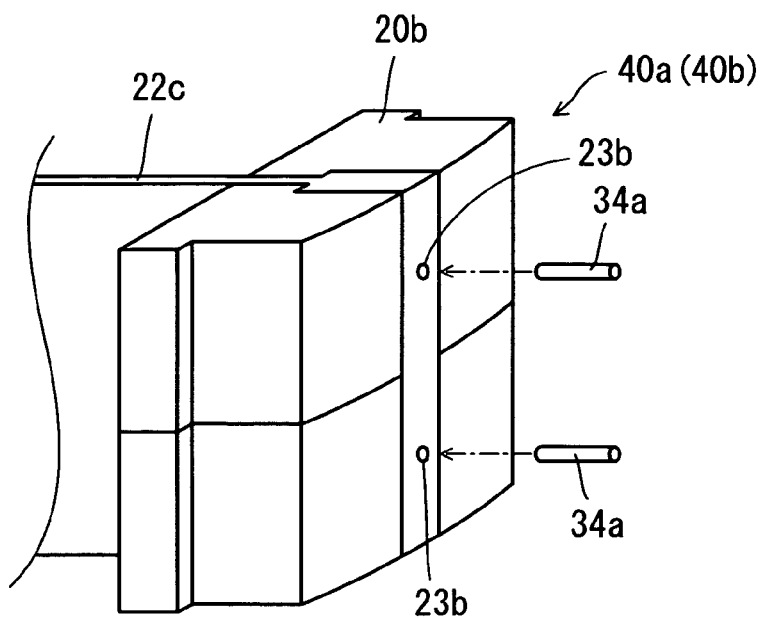

FIG. 7
(a)
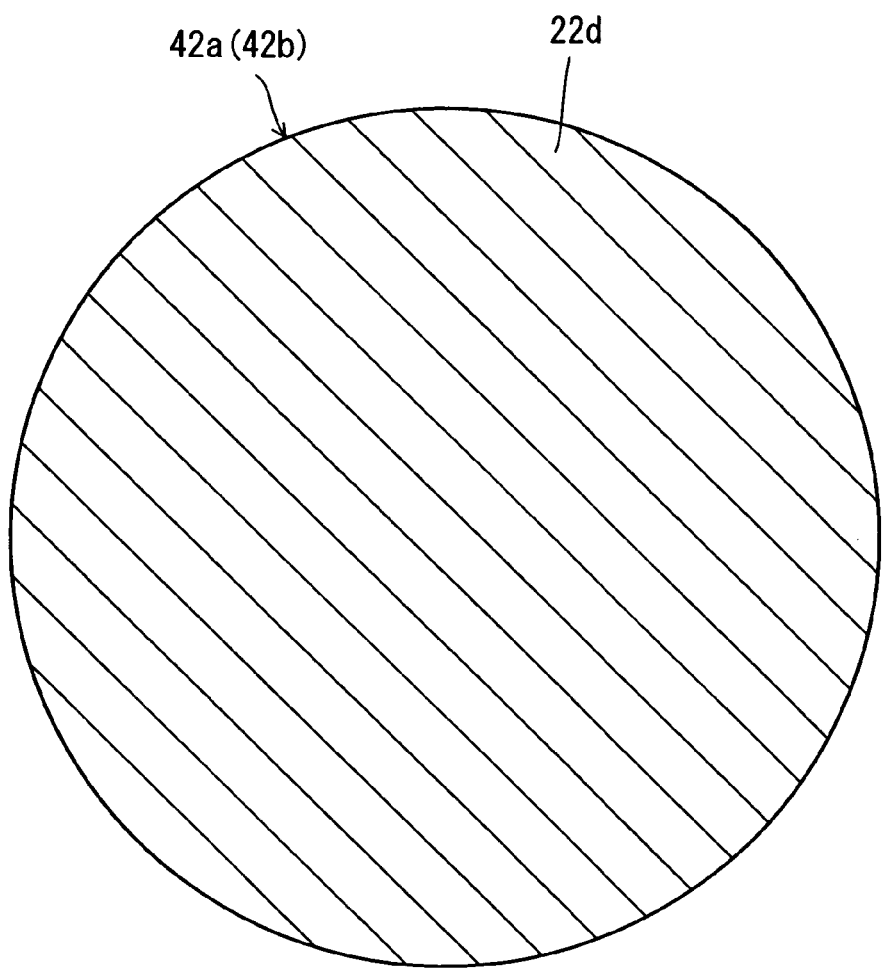
(b)
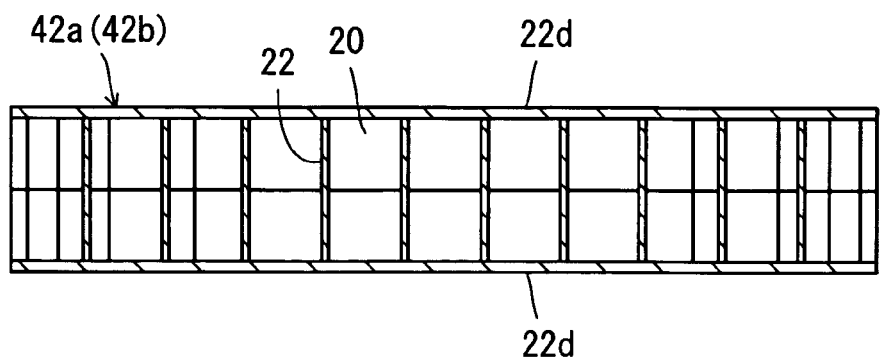

FIG. 8
(a)
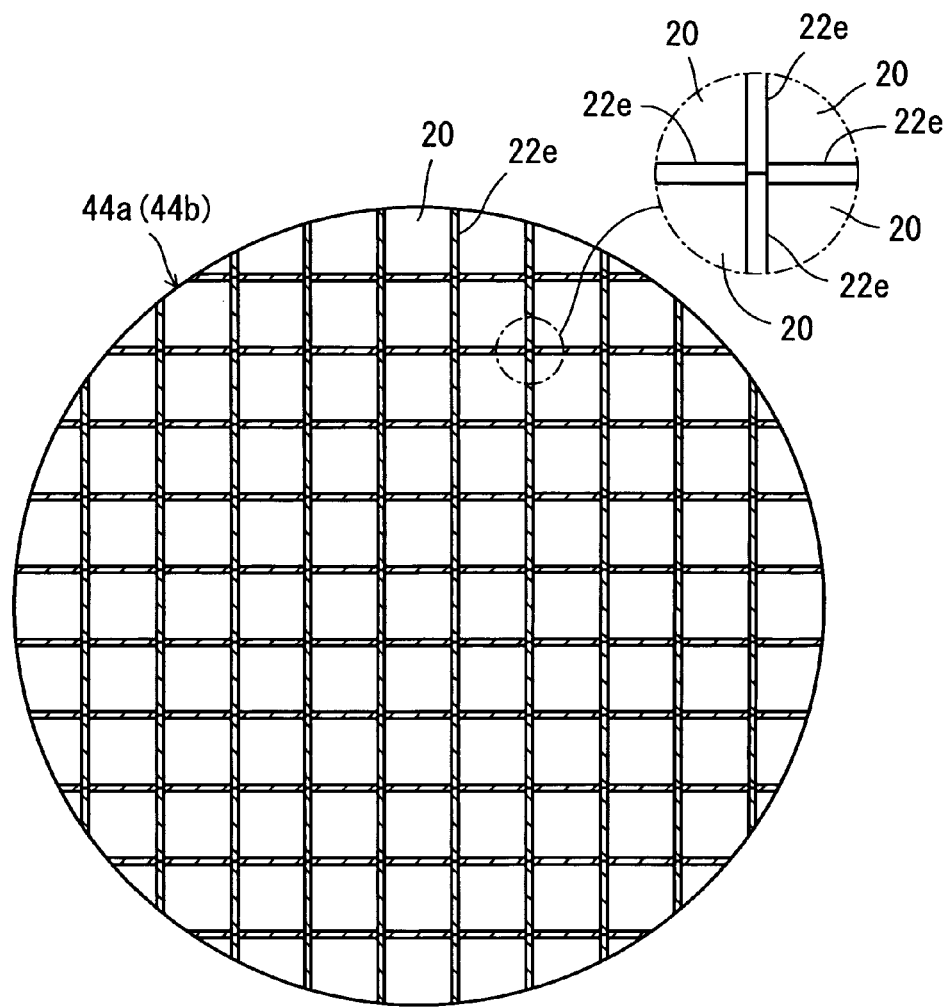
(b)
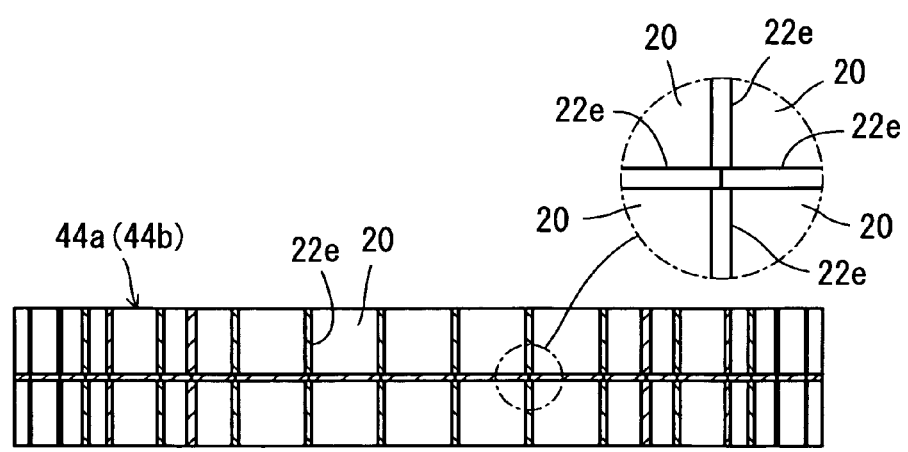

FIG. 9
(a)
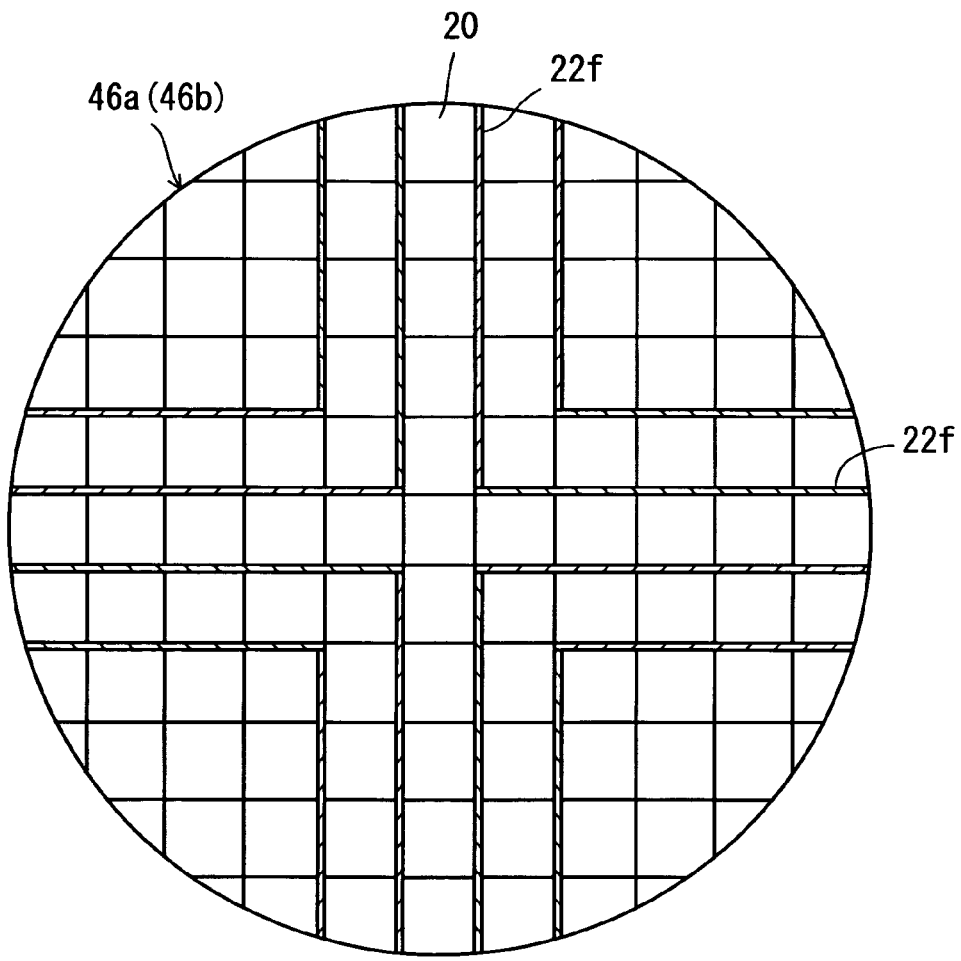
(b)
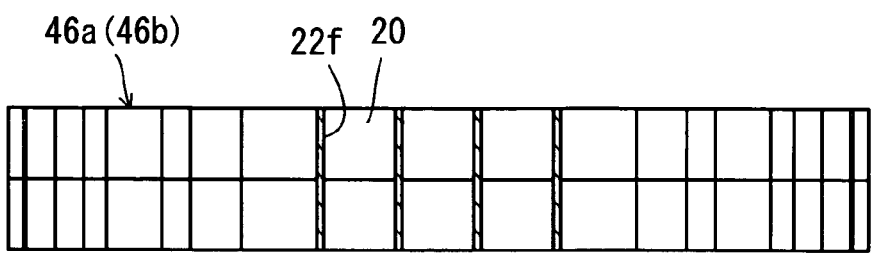

F I G. 1 1
(a)
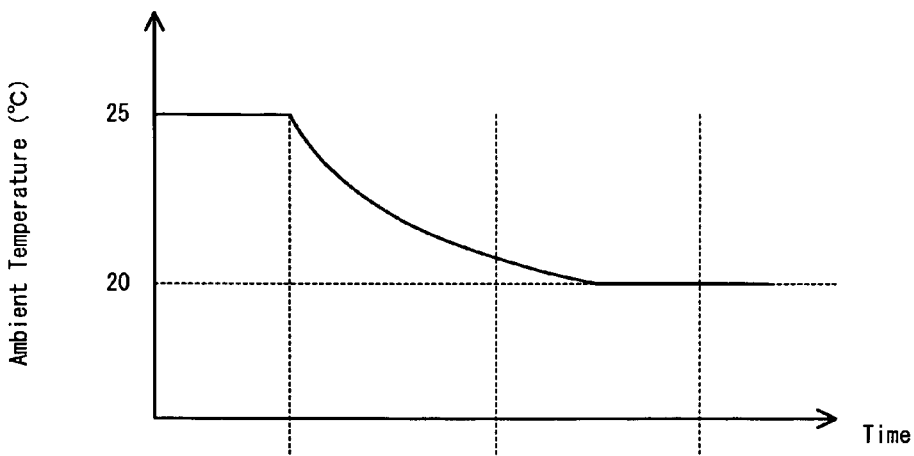
(b)
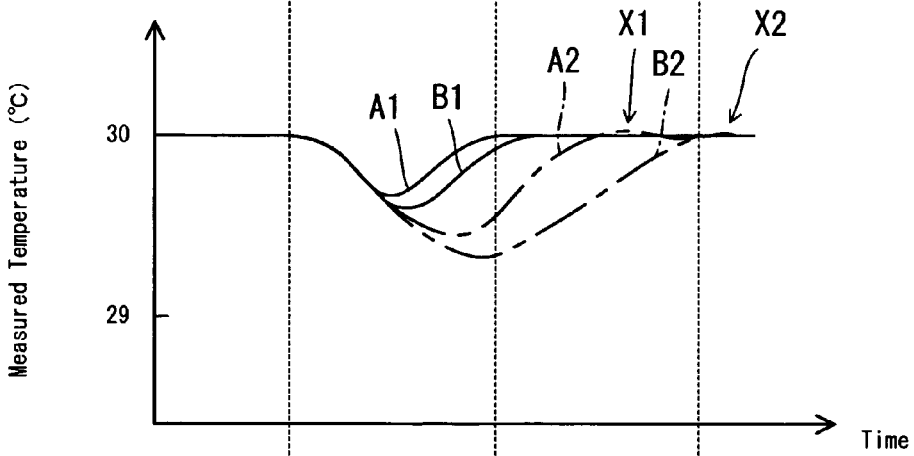
(c)
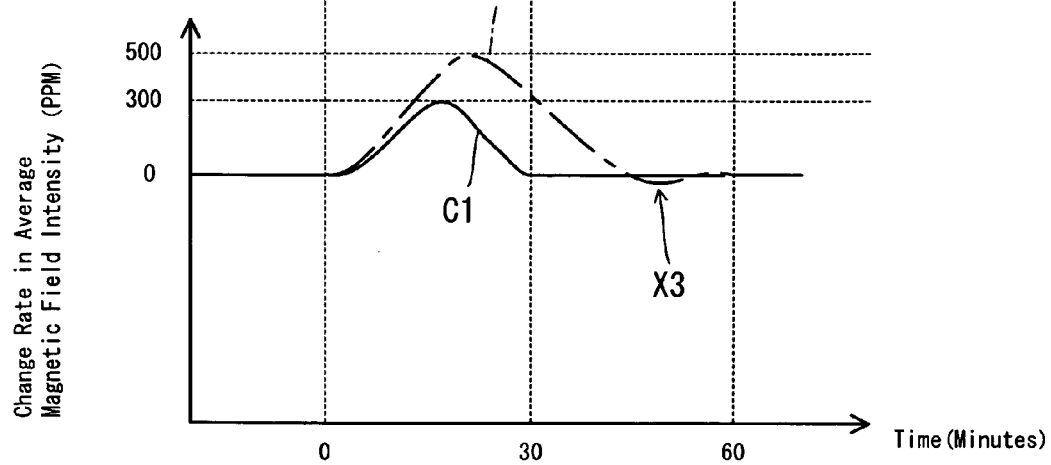

F I G. 1 6
(a)
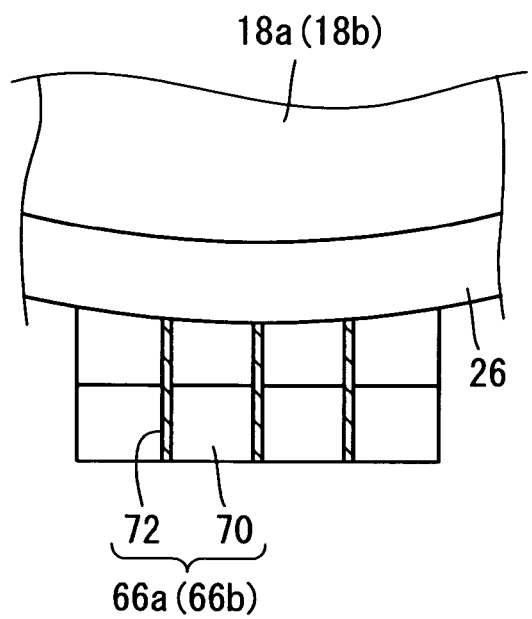
(b)
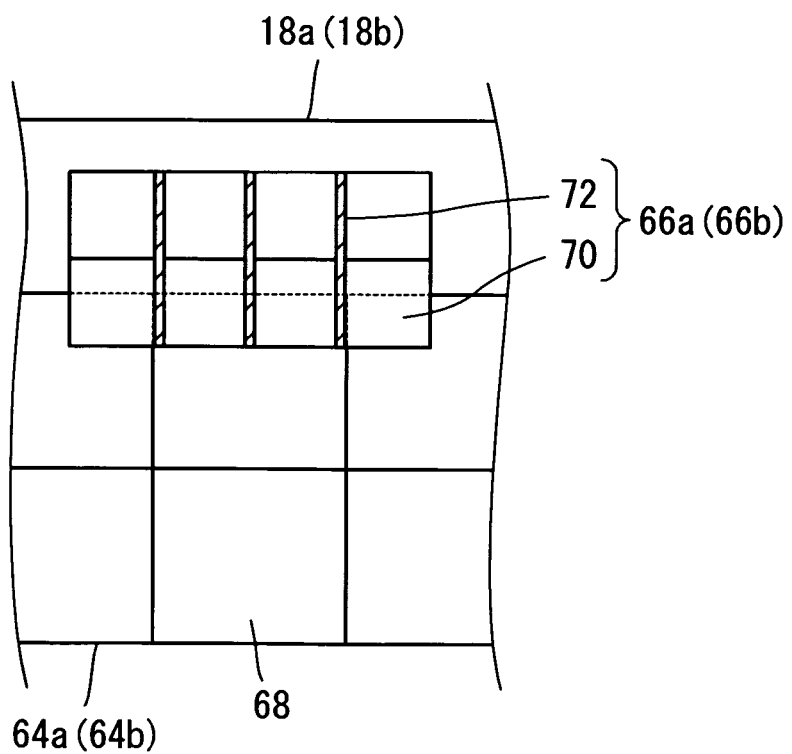

F I G. 1 7
(a)
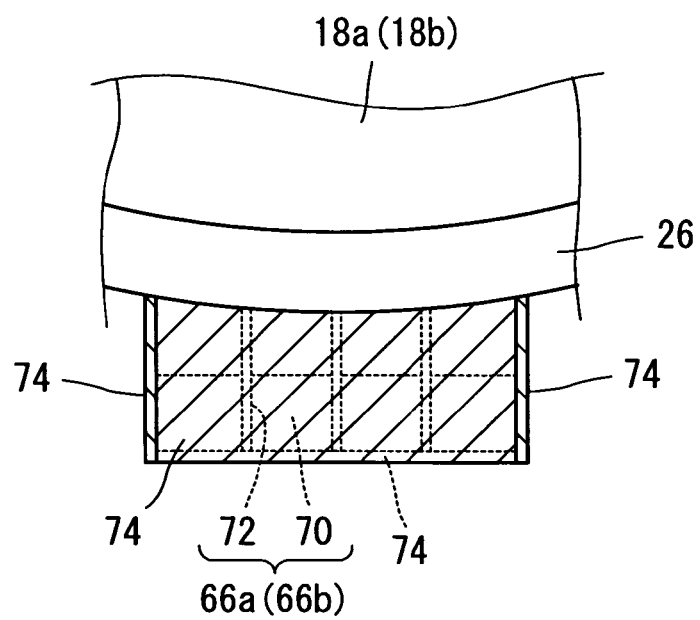
(b)
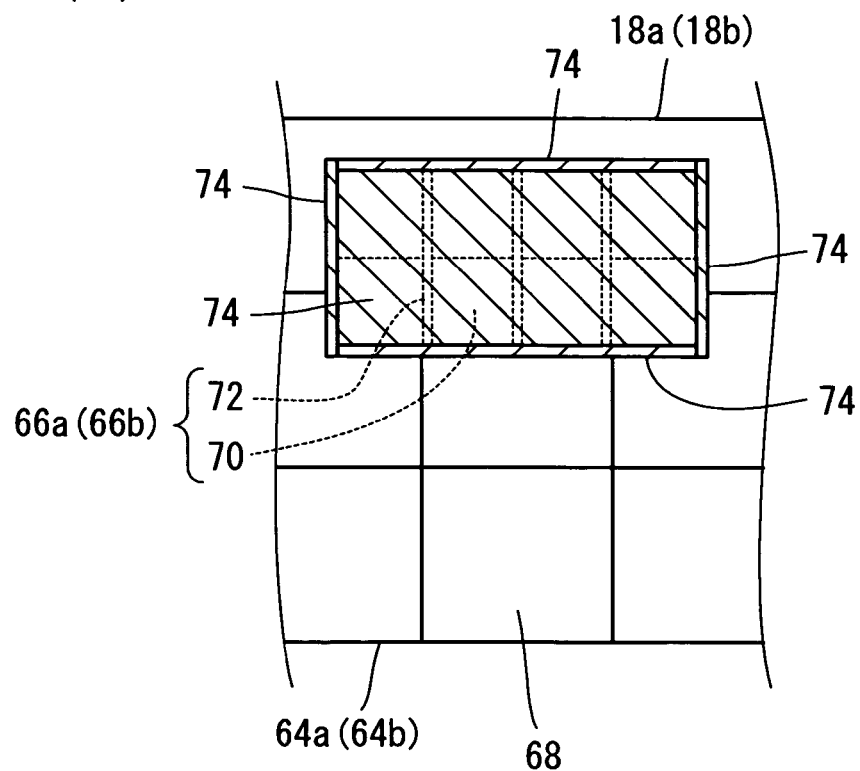

FIG. 23
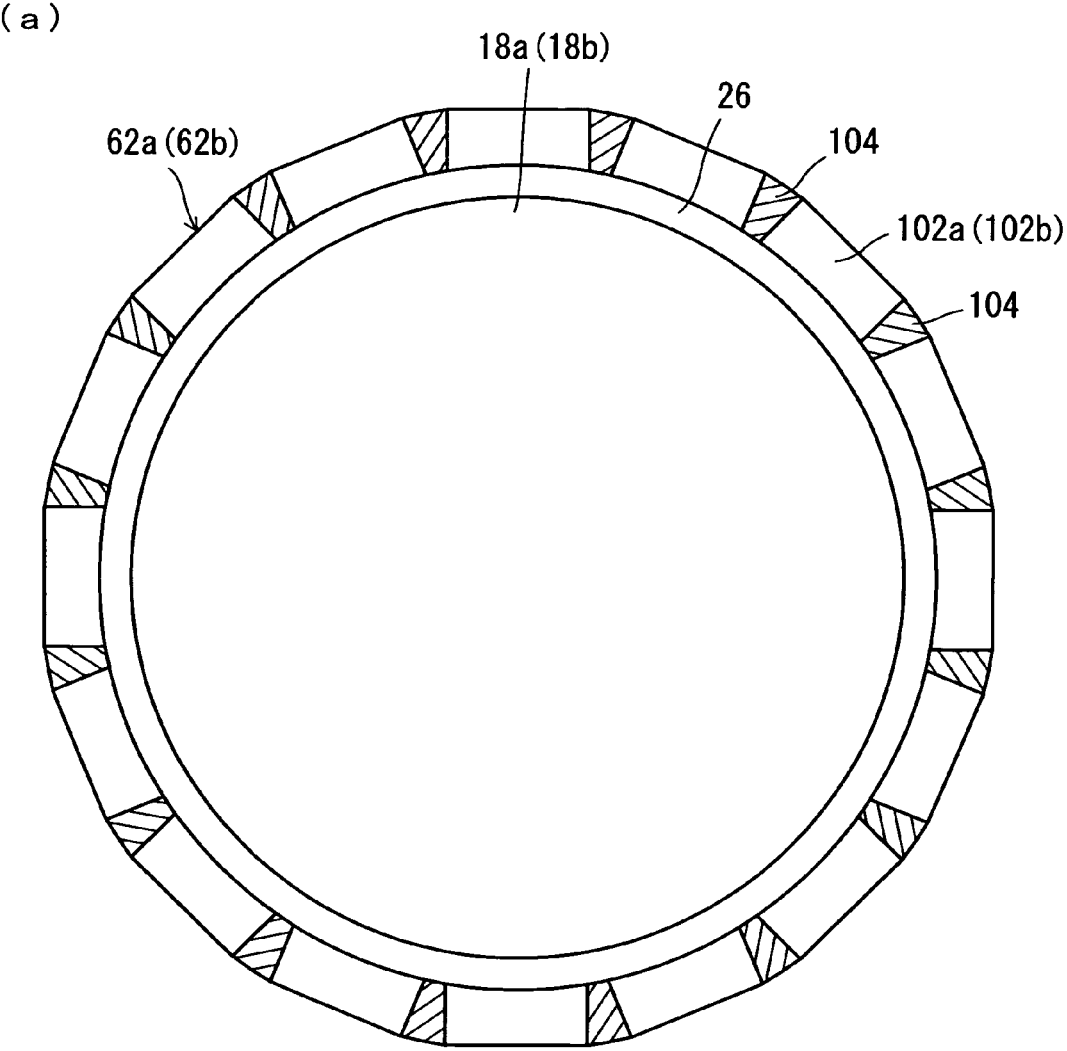
(a)
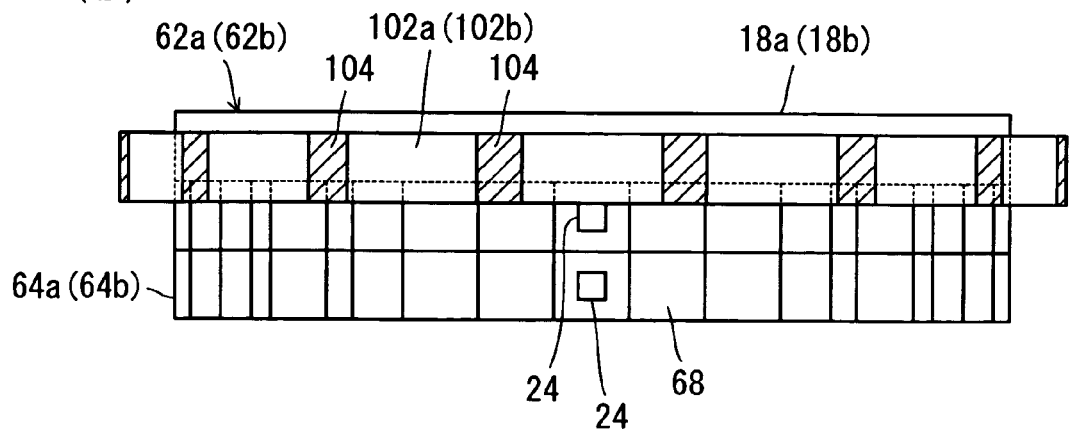
(b)

FIG. 25
(a)
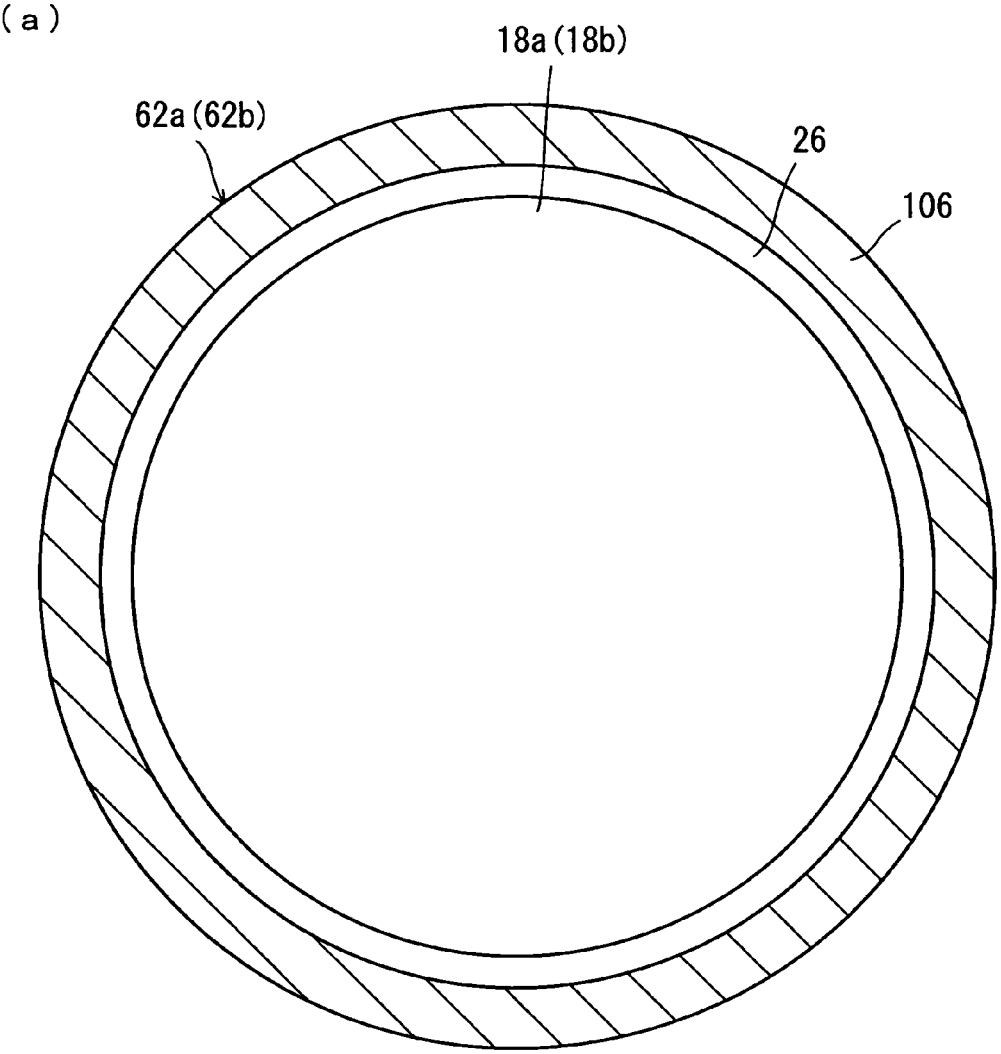
(b)
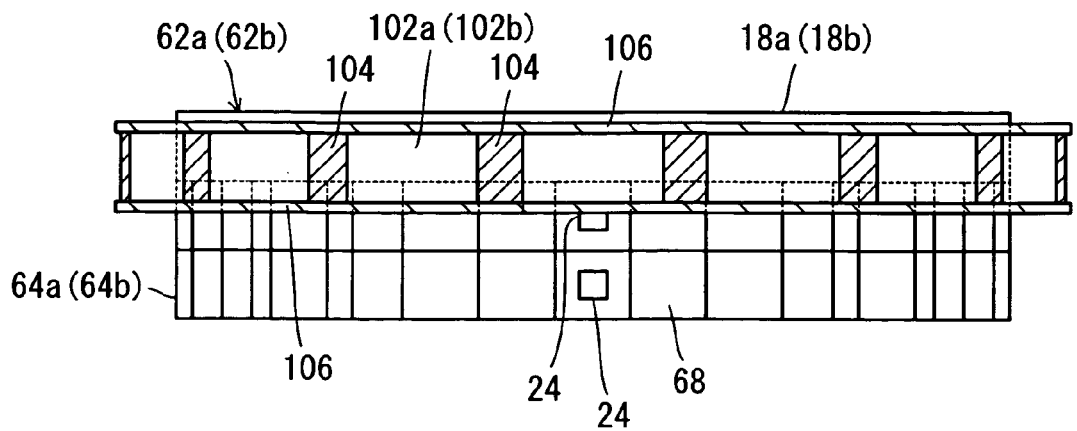

FIG. 26
(a)
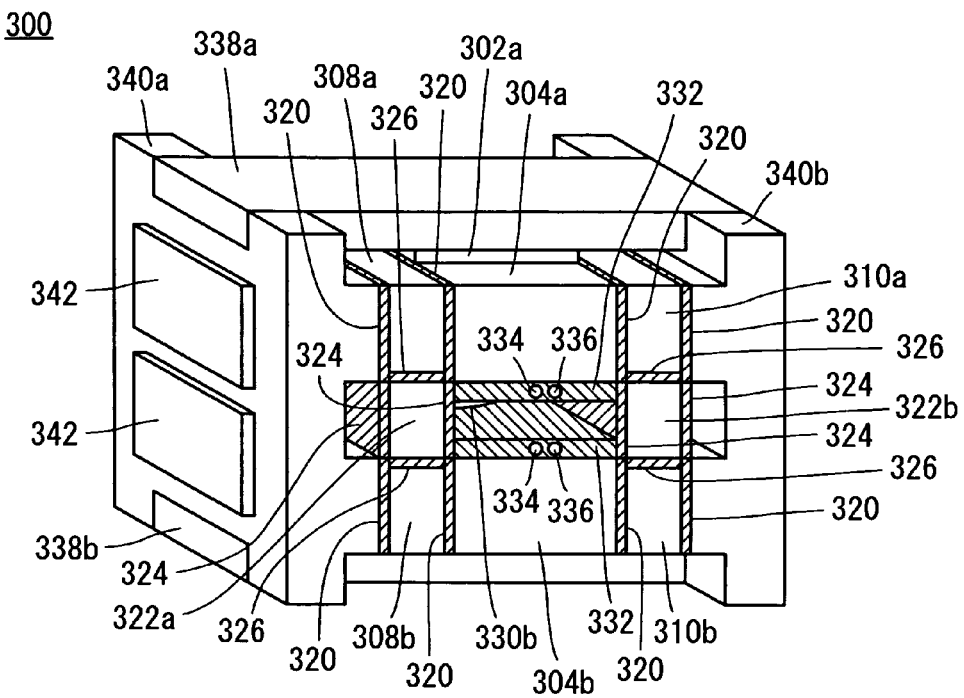
(b)
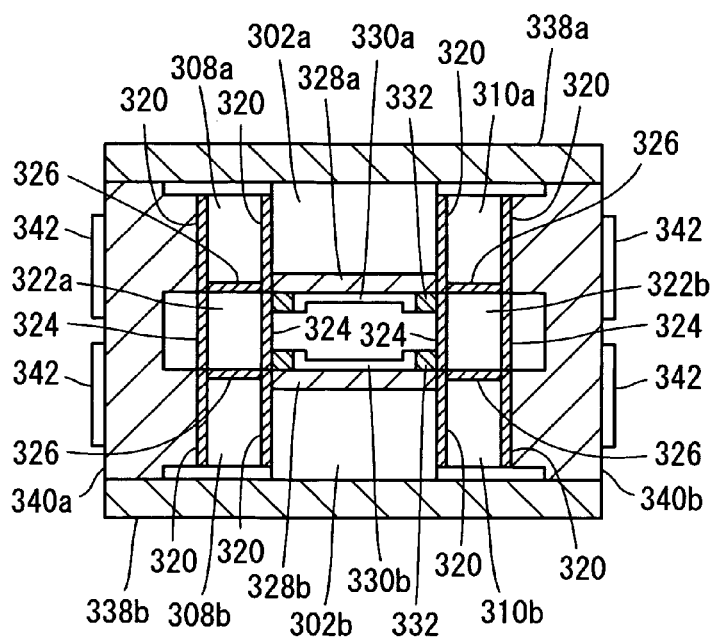
(c)
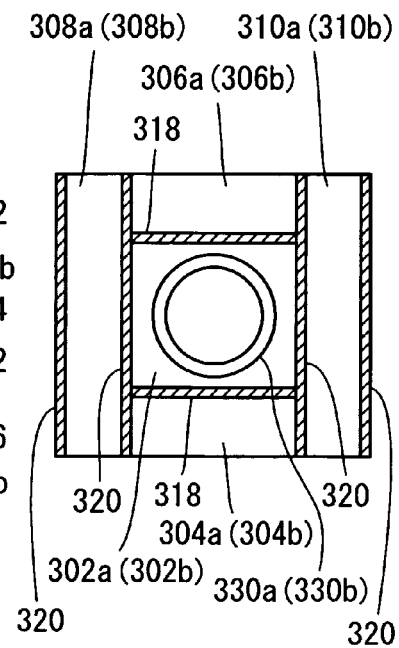

FIG. 28  PRIOR ART
(a)
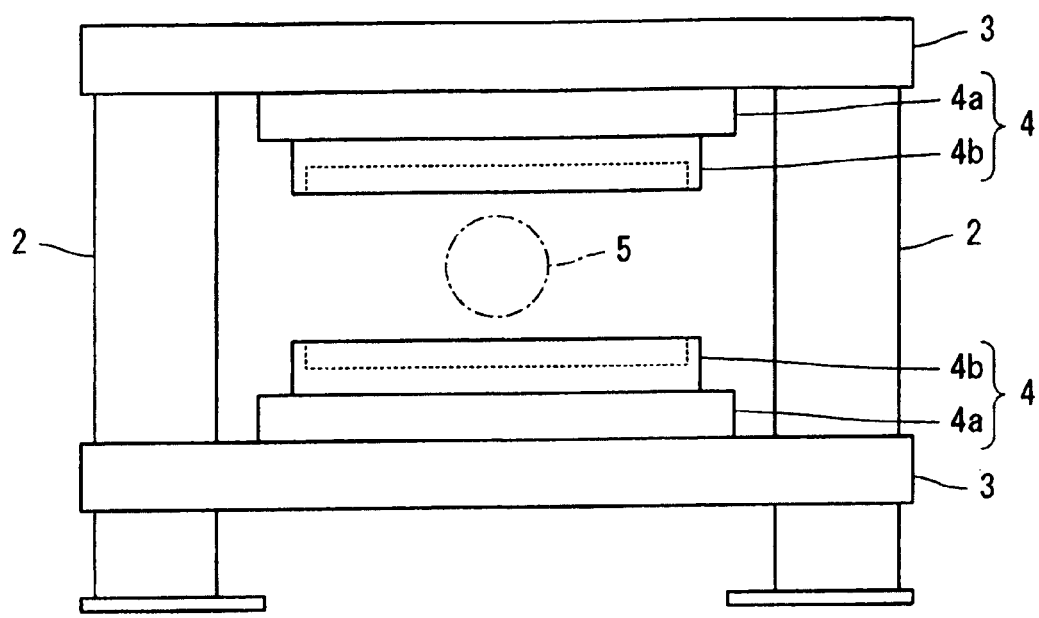
(b)
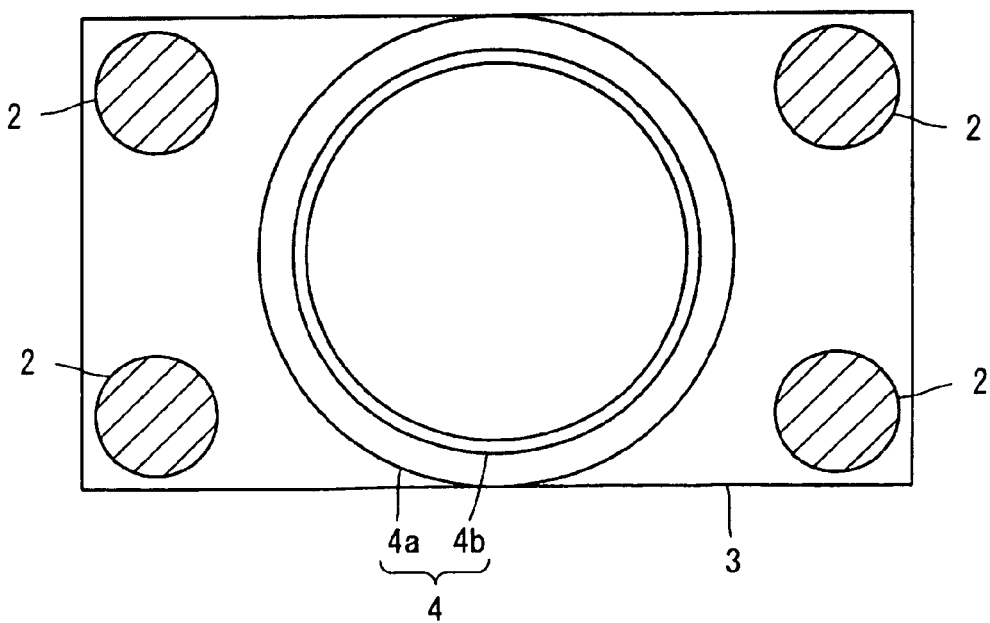

MAGNETIC FIELD GENERATOR

TECHNICAL FIELD

The present invention relates to magnetic field generators, and more specifically to permanent magnet type magnetic field generators used in MRI (Magnetic Resonance Imaging) apparatuses, etc.

BACKGROUND ART

Conventionally, MRI apparatuses, etc. are known as an apparatus in which a specimen is placed in a magnetic field (static magnetic field) generated by a magnetic field generator and tomographic images of the specimen is obtained.

FIG. 28 shows a magnetic field generator 1 as an example of the magnetic field generator used in an MRI apparatus. The magnetic field generator 1 includes a pair of plate yokes 3 which are connected with each other by four column yokes 2, to face each other with a space in between. The opposed surfaces of the plate yokes 3 are each provided with a magnetic pole 4. Each magnetic pole 4 includes a permanent magnet group 4a fixed on the opposed surface of the plate yoke 3 and a pole piece 4b fixed on an opposed surface of the permanent magnet group 4a. The permanent magnet group 4a is made of a plurality of unillustrated permanent magnets. Using the permanent magnet group 4a in this way as the source of magnetic field generation enables to reduce running cost as compared to cases in which the magnetic field is generated by supplying electric power to electric magnets. It is also possible to reduce the size of the apparatus since there is no need for an electric power supply apparatus, etc. for driving the electric magnets.

In order to obtain clear tomographic images, the magnetic field generator 1 must be able to generate, within a magnetic field space 5 in its space, a magnetic field which has a uniformity accuracy within $1\times10^{-4}$ (within 100 PPM) in a range of 0.02 T through 3.0 T. However, the permanent magnet group 4a recently is often made of Nd—Fe—B sintered magnets, which has a residual magnetic flux density temperature coefficient of $-0.1\%/°C$. approx: Magnetic characteristics change with temperature change, so it is difficult to create a uniform magnetic field of a desired intensity. In an attempt to overcome this problem, there is prevailed a technique as shown in FIG. 29, of covering the four column yokes 2 and the pair of plate yokes 3 where the magnetic poles 4 are provided, with a heat insulation member 6 thereby reducing the temperature change caused by changes in ambient temperature in each element (particularly the permanent magnet group 4a) of the magnetic field generator 1.

Also, there is prevailed a technique of employing a heater in addition to the heat insulation member 6 to maintain the permanent magnet group 4a at a constant temperature. As an example, Patent Document 1 for example discloses a technique of providing a surface heater on an inner surface of the heat insulation member 6 and moving the warmed air in the heat insulation member 6 by a fan. Also, Patent Document 2 discloses a technique of providing a surface heater on a surface facing away from the opposed surface in each of the pair of plate yokes 3. Further, Patent Document 3 discloses a technique of providing a surface heater on each side surface of the plate yokes 3. However, the technique according to Patent Document 1 poses a problem of complication in apparatuses related to temperature control since the air must be forced to move by the fan. In addition, use of air as a heat transfer medium poses another problem that the heat generated by the surface heater is not transferred efficiently to the permanent magnet group 4a. The techniques according to Patent Documents 2 and 3 also have the problem of inefficient transfer of heat generated by the surface heater, to the permanent magnet group 4a because the heat diffuses from a surface of the surface heater facing away from the surface that makes contact with the plate yoke 3.

In an attempt to solve these kinds of problems, Patent Document 4 discloses a technique of providing a heater inside the permanent magnet group 4a or the plate yokes 3, etc. The technique according to Patent Document 4 enables to reduce diffusion of heat from the heater to outside.

Patent Document 1: JP-A 63-43649
Patent Document 2: JP-A 63-278310
Patent Document 3: JP-A 8-266506
Patent Document 4: WO 99/65392

DISCLOSURE OF THE INVENTION

Problems to be Solved by the Invention

A problem, however, according to the technique in Patent Document 4 is that heat does not reach easily to places far from the heater, leading to poor temperature following ability and temperature controllability of the elements of the magnetic field generator which are disposed far from the heater with respect to the heat generated by the heater. As another problem, the amount of heat delivered to the elements of the magnetic field generator varies widely depending on the distance from the heater, leading to uneven heating among the elements of the magnetic field generator and nonuniform temperature distribution. Generally, carbon steel and cast iron used as the column yokes 2 and the plate yokes 3 have a thermal conductivity of 75 W/m·K approx. On the contrary, Nd—Fe—B sintered magnets have a thermal conductivity of 9 W/m·K approx, i.e. lower than the thermal conductivity of the column yokes 2 and of the plate yokes 3. Further, in the permanent magnet group 4a, mutually adjacent permanent magnets are bonded to each other by an adhesive which has a low thermal conductivity. Thus, these problems are likely to affect the permanent magnet group 4a in particular, and there has been a risk of not being able to generate a uniform magnetic field of a desired intensity.

If many heaters are used to improve temperature following ability and temperature controllability or to decrease nonuniform temperature distribution, the apparatus will become complicated, power consumption for heater operation will be increased, and running cost will be increased.

Therefore, a primary object of the present invention is to provide a magnetic field generator capable of generating a uniform magnetic field of a desired intensity easily and stably without increasing running cost.

Means for Solving the Problems

According to an aspect of the present invention, there is provided a magnetic field generator which includes a pair of magnetic poles each including a first permanent magnet group having a plurality of permanent magnets, and a pole piece provided on an end surface of the first permanent magnet group. The pole pieces are faced to each other with a space in between. The magnetic field generator further includes: heating means for supplying heat to at least the pair of magnetic poles; and a heat conducting member provided between mutually adjacent permanent magnets at least in part of the first permanent magnet group.

According to the present invention, heat generated by the heating means is conducted uniformly and quickly by heat conducting member which is provided between mutually adjacent permanent magnets in the first permanent magnet group to the adjacent permanent magnets in the first permanent magnet group. Therefore, the magnetic field generator has a superb temperature following ability and heat controllability, and it is possible to maintain the first permanent magnet group at a constant temperature easily and uniformly, and to generate a uniform magnetic field of a desired intensity stably. Further, since heat is easily conducted to the first permanent magnet group, it is possible to reduce energy necessary to drive the heating means so running cost does not increase.

According to another aspect of the present invention, there is provided a magnetic field generator which includes a pair of magnetic poles each including a first permanent magnet group having a plurality of permanent magnets, a pole piece provided on an end surface of the first permanent magnet group, and a second permanent magnet group including a plurality of permanent magnets and provided on an outer side surface of the pole piece. The pole pieces are faced to each other with a space in between. The magnetic field generator further includes: heating means for supplying heat to at least the pair of magnetic poles; and a heat conducting member provided between mutually adjacent permanent magnets at least in part of the second permanent magnet group.

There is already known a magnetic field generator which includes a pair of pole pieces each having its outer side surface provided with a second permanent magnet group for prevention of magnetic flux leakage. In such a magnetic field generator, the second permanent magnet group which is placed closely to the space is subject to temperature change associated with ambient temperature change, as compared to the first permanent magnet group. According to the present invention, heat generated by the heating means is conducted uniformly and quickly by the heat conducting member which is provided between mutually adjacent permanent magnets in the second permanent magnet group to the adjacent permanent magnets in the second permanent magnet group. Therefore, it is possible to maintain the second permanent magnet group which is sensitive to the ambient temperature at a constant temperature easily and uniformly, and to generate a uniform magnetic field of a desired intensity stably. Further, since heat is easily conducted to the second permanent magnet group, it is possible to reduce energy necessary to drive the heating means so running cost does not increase.

According to another aspect of the present invention, there is provided a magnetic field generator which includes a pair of magnetic poles each including a first permanent magnet group having a plurality of permanent magnets, a pole piece provided in an end surface of the first permanent magnet group, and a plurality of second permanent magnet groups each including a plurality of permanent magnets and provided on an outer side surface of the pole piece. The pole pieces are faced to each other with a space in between. The magnetic field generator further includes: heating means for supplying heat to at least the pair of magnetic poles; and a heat conducting member provided between mutually adjacent second permanent magnet groups at least in part of the second permanent magnet groups.

According to the present invention, heat generated by the heating means is conducted by the heat conducting member provided between mutually adjacent second permanent magnet groups to these mutually adjacent second permanent magnet groups uniformly and quickly. Therefore, it is possible to maintain the second permanent magnet group which is sensitive to the ambient temperature at a constant temperature easily and uniformly. Further, it is possible to reduce temperature difference between mutually adjacent second permanent magnet groups, and to generate a uniform magnetic field of a desired intensity stably. Since heat is easily conducted to the second permanent magnet group, it is possible to reduce energy necessary to drive the heating means so running cost does not increase. Further, the arrangement is simple placement of a heat conducting member between mutually adjacent second permanent magnet groups. This enables to reduce the number of parts in the magnetic field generator and to reduce the number of manufacturing steps, as compared to a case where a heat conducting member is provided between mutually adjacent permanent magnets in the second permanent magnet group.

It should be noted here that the term "heat conducting member" means a member which has a thermal conductivity higher than the thermal conductivity of at least the first permanent magnet group and the second permanent magnet group.

Preferably, the magnetic field generator includes a heat conducting member provided on at least part of a surface of the second permanent magnet group. By providing a heat conducting member also on the surface of the second permanent magnet group as described, heat generated by the heating means is conducted more uniformly and quickly to the second permanent magnet group. Therefore, it becomes possible to generate a uniform magnetic field of a desired intensity more stably.

Further preferably, heating means is buried in the heat conducting member. By burying a heating means in the heat conducting member, heat generated by the heating means is conducted to the heat conducting member without diffusing to the outside, and therefore it becomes possible to deliver heat more quickly and efficiently to the permanent magnet group. Further, since heat is conducted to the permanent magnet group more easily, it becomes possible to further reduce energy necessary to drive the heating means and to reduce running cost.

Further preferably, the magnetic field generator includes a coating material formed on at least part of the permanent magnets and having a thermal conductivity not lower than 150 W/m·K. By forming a coating material on the permanent magnets as described, heat generated by the heating means is conducted more uniformly and quickly by the coating material to the permanent magnets and thus to the permanent magnet group. Therefore, it becomes possible to generate a uniform magnetic field of a desired intensity more stably.

Further preferably, the magnetic field generator includes a temperature sensor disposed near the heating means. By disposing a temperature sensor near the heating means as described, it becomes possible to sense the heat generated by the heating means quickly and to prevent the heating means from generating an unnecessary amount of heat. In particular, when the heating means is disposed in or near a permanent magnet group, thermal demagnetization can occur in the permanent magnets if the amount of heat generated by the heating means becomes excessively large. However, this can be prevented by placing a temperature sensor near the heating means.

Further preferably, the magnetic field generator includes a heat insulation material which covers the permanent magnet group. By covering the permanent magnet group with a heat insulation material as described, temperature change in the permanent magnet group caused by changes in the ambient temperature is reduced. Therefore, it becomes possible to maintain the permanent magnet group at a constant temperature more stably. Further, since heat diffusion from the permanent magnet group to the outside becomes less, and the temperature decrease of the permanent magnet group becomes less, it becomes possible to further reduce energy necessary to drive the heating means and to reduce running cost. The heat insulation material is suitably provided by, for example, a vacuum insulation material in the form of a vacuum pack of a core material made of inorganic fiber heat insulation material such as glass wool or foamed plastic heat insulation material such as foamed polystyrene and foamed urethane into a package made of a metal film, etc. which has a good gas insulation capability.

Further preferably, the magnetic field generator includes a heat storage member which covers the permanent magnet group. In this case, the heat storage member holds the heat of the permanent magnet group, and when the temperature of the permanent magnet group decreases, heat held in the heat storage member is conducted to the permanent magnet group. Therefore, it is possible to maintain the permanent magnet group at a constant temperature more stably. Further, since the heat is conducted from the heat storage member to the permanent magnet group when the temperature of the permanent magnet group decreases, it becomes possible to further reduce energy necessary to drive the heating means and to reduce running cost. Heat storage material included in the heat storage member is suitably provided by an inorganic hydrated salt which has a large heat storage capacity and can hold heat stably.

BRIEF DESCRIPTION OF THE DRAWINGS

FIG. 3 An example of permanent magnet group provided on an opposed surface of a plate yoke: FIG. 3(a) is a schematic plan view whereas FIG. 3(b) is a schematic side view.

FIG. 4 A disposition mode of a surface heater in the permanent magnet group in FIG. 3: FIG. 4(a) is a schematic plan view whereas FIG. 4(b) is a schematic side view.

FIG. 6 A primary portion of another permanent magnet group which includes a heat conducting member in which tubular heaters are buried. FIG. 6(a) is a schematic perspective view of the permanent magnet group, with the tubular heaters buried into an end portion of the heat conducting member extended along a side surface of the permanent magnet. FIG. 6(b) is a schematic perspective view of the permanent magnet group, with the tubular heaters buried into a thickened end portion of the heat conducting member.

FIG. 7 Another example of the permanent magnet group provided on the opposed surface of the plate yoke. FIG. 7(a) is a schematic plan view whereas FIG. 7(b) is a schematic side view.

FIG. 8 Another example of the permanent magnet group provided on the opposed surface of the plate yoke. FIG. 8(a) is a schematic plan view whereas FIG. 8(b) is a schematic side view.

FIG. 9 Another example of the permanent magnet group provided on the opposed surface of the plate yoke. FIG. 9(a) is a schematic plan view whereas FIG. 9(b) is a schematic side view.

FIG. 11 Shows graphs depicting an experimental condition and an experimental result. FIG. 11(a) shows a time course observation of an ambient temperature, FIG. 11(b) shows a time course observation of the temperature of a permanent magnet group, and FIG. 11(c) shows a time course observation of a change rate in an average magnetic field intensity.

FIG. 16 An example of permanent magnet group provided on an outer side surface of the pole piece. FIG. 16(a) is a schematic plan view whereas FIG. 16(b) is a schematic side view.

FIG. 17 A disposition mode of a heat conducting member covering a surface of the permanent magnet group in FIG. 16. FIG. 17(a) is a schematic plan view whereas FIG. 17(b) is a schematic side view.

FIG. 23 A disposition mode of heat conducting members in a plurality of permanent magnet groups provided on an outer side surface of the pole piece. FIG. 23(a) is a schematic plan view whereas FIG. 23(b) is a schematic side view.

FIG. 25 A disposition mode of a heat conducting member covering end surfaces of a plurality of permanent magnet groups provided on an outer side surface of the pole piece. FIG. 25(a) is a schematic plan view whereas FIG. 25(b) is a schematic side view.

FIG. 26 Another embodiment of the present invention. FIG. 26(a) is a schematic perspective view, FIG. 26(b) is a schematic sectional view, and FIG. 26(c) is a schematic plan view of a primary portion.

FIG. 28 A conventional magnetic field generator. FIG. 28(a) is a schematic front view whereas FIG. 28(b) is a schematic plan view FIG. 29 A schematic perspective view of a conventional magnetic field generator.

Figure 1:
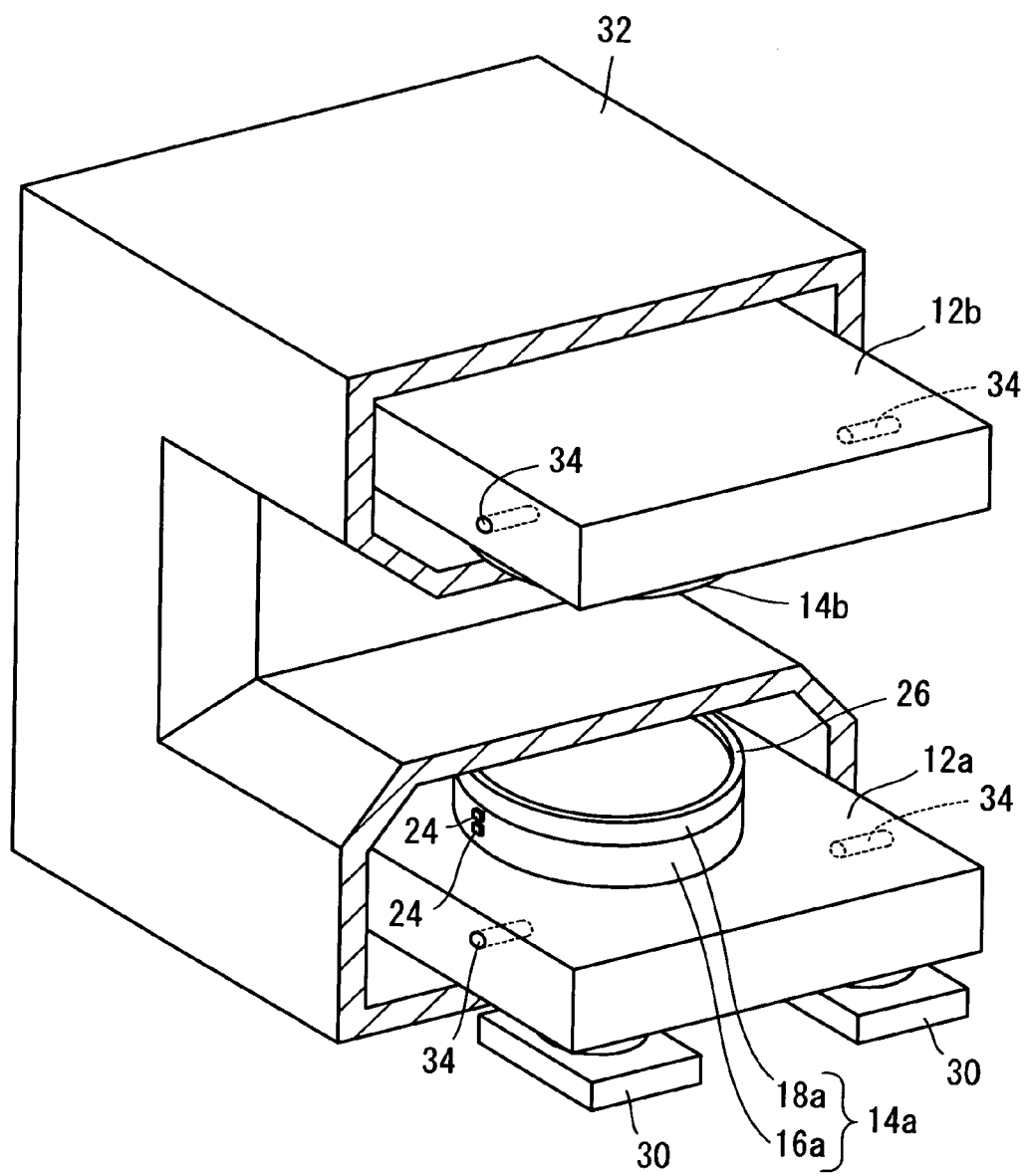
FIG. 1 A schematic perspective view of an embodiment of the present invention.

LEGEND 10, 10a, 10b, 10c, 10d, 10e, 10f, 10g, 200, 300 Magnetic field generators
12a, 12b, 338a, 338b Plate yokes
14a, 14b, 62a, 62b, 202a, 202b Magnetic poles
16a, 16b, 36a, 36b, 38a, 38b, 40a, 40b, 42a, 42b 44a, 44b, 46a, 46b, 64a, 64b, 66a, 66b, 102a, 102b, 204a, 204b, 302a, 302b, 304a, 304b, 306a, 306b, 308a, 308b, 310a, 310b, 322a, 322b Permanent magnet groups
18a, 18b, 330a, 330b Pole pieces
20, 20a, 20b, 68, 70, 206, 314 Permanent magnets 22, 22a, 22b, 22c, 22d, 22e, 22f, 72, 74, 104, 104a, 106, 316, 318, 320, 324, 326, 332 Heat conducting members 24, 336 Temperature sensors 34, 34a, 34b, 334 Tubular heaters 35, 342 Surface heaters 48a, 48b, 76a, 76b, 80a, 80b Vacuum insulation materials 56a, 56b, 90a, 90b, 92a, 92b Heat storage members 312 Coating material

BEST MODE FOR CARRYING OUT THE INVENTION

Hereinafter, embodiments of the present invention will be described with reference to the drawings.

Figure 2:
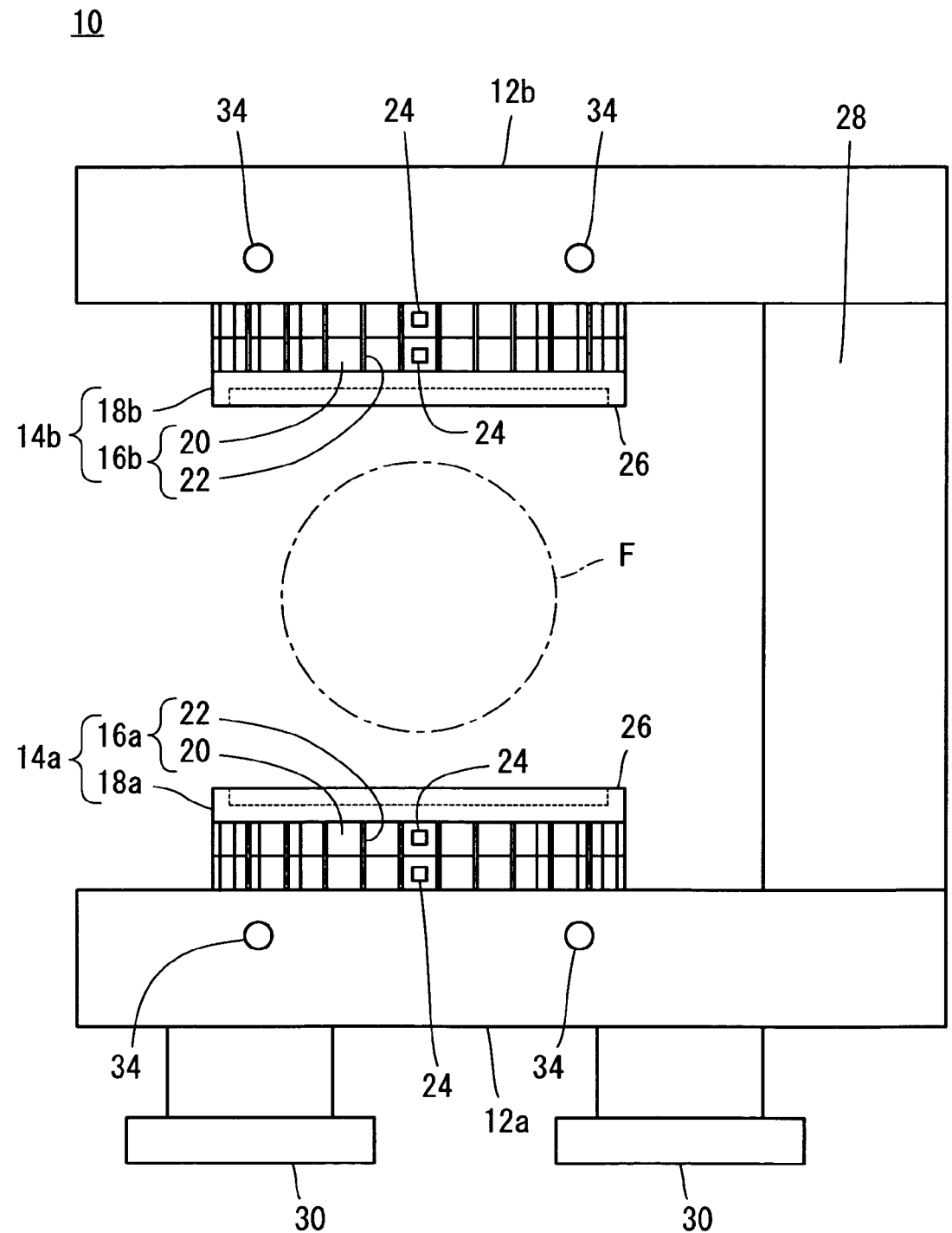
FIG. 2 A schematic side view of the embodiment in FIG. 1.

Referring to FIG. 1 and FIG. 2, a magnetic field generator 10 according to an embodiment of the present invention is a magnetic field generator for an open type MRI apparatus, and includes a pair of plate yokes 12a, 12b opposed to each other with a space in between and a pair of magnetic poles 14a, 14b.

The magnetic pole 14a includes a permanent magnet group 16a and a pole piece 18a. Likewise, the magnetic pole 14b includes a permanent magnet group 16b and a pole piece 18b. The permanent magnet group 16a is fixed on a surface which is faced to the plate yoke 12b, of the plate yoke 12a. Likewise, the permanent magnet group 16b is fixed on a surface which is faced to the plate yoke 12a, of the plate yoke 12b. The pole piece 18a is fixed on a surface which is faced to the permanent magnet group 16b, of the permanent magnet group 16a. Likewise, the pole piece 18b is fixed on a surface which is faced to the permanent magnet group 16a, of the permanent magnet group 16b. As understood from FIG. 2, in the pair of magnetic poles 14a, 14b as described, the pole pieces 18a, 18b are opposed to each other, with a space in between. Also, as shown in FIG. 2, each of the permanent magnet groups 16a, 16b includes a plurality of permanent magnets 20 and a plurality of heat conducting members 22.

As understood from FIG. 3(a) and FIG. 3(b), the permanent magnet group 16a is an integral body of a plurality of permanent magnets 20 and a plurality of heat conducting members 22, formed substantially in a disc-like shape. In the permanent magnet group 16a, the heat conducting members 22 are disposed between the permanent magnets 20 which are adjacent to each other in a predetermined direction [a left-right direction in FIG. 3(a) and FIG. 3(b)], and extend in a predetermined direction [a top-bottom direction in FIG. 3(a)], making a stripe disposition pattern in an end view.

Those permanent magnets 20 which form a circumferential edge of the permanent magnet group 16a have a curved outer side surface so as to give the permanent magnet group 16a a circular section, and a height of 50 mm approx. The other permanent magnets 20 which form the rest of the permanent magnet group 16a are formed as rectangular parallelepiped (substantially cubic), with both end surfaces (the upper surface and the lower surface) having four sides each measuring 50 mm approx, and a height measuring 50 mm approx. The heat conducting member 22 are platy, having a thickness of 0.35 mm approx. and a height of 100 mm approx.

As shown in FIG. 3(b), the permanent magnet group 16a is formed by two tiers of the permanent magnets 20, and thus has a height of 100 mm approx. In the permanent magnet group 16a which is fixed on the plate yoke 12a, each permanent magnet 20 and each heat conducting member 22 which face the opposed surface of the plate yoke 12a make contact with the opposed surface of the plate yoke 12a (See FIG. 2). The permanent magnet group 16b is the same as the permanent magnet group 16a, and is disposed in the same manner as the permanent magnet group 16a, but on the opposed surface of the plate yokes 12b.

It should be noted here that in the present embodiment, the permanent magnet groups 16a, 16b are formed substantially in a disc-like shape (so they have a circular section); however, the shape of the permanent magnet groups 16a, 16b is discretional. Note further, that FIG. 3(a) and FIG. 3(b) show the heat conducting member 22 much thicker than the actual for easier understanding.

The permanent magnets 20 used in the permanent magnet groups 16a, 16b are provided by a high saturation magnetic flux density type Nd—Fe—B sintered magnet for example. The permanent magnets 20 have a thermal conductivity of 9 W/m·K approx. The permanent magnets 20 as described are built with a plurality of unillustrated individual magnets, which are bonded together with adhesive, etc. The heat conducting members 22 are made of aluminum for example. The heat conducting members 22 have a thermal conductivity not lower than 150 W/m·K.

As shown in FIG. 3(a), the permanent magnet group 16a is provided with temperature sensors 24 on its side surface along its diameter as in an end view. As shown in FIG. 3(b) in a side view, the temperature sensors 24 are attached to the side surface of the permanent magnet group 16a, one on a permanent magnet 20 in the lower tier, and the other on a permanent magnet 20 right above in the upper tier. The permanent magnet group 16b also is provided with temperature sensors 24 in the same manner as described. The temperature sensors 24 are controlled by an unillustrated controller, and temperatures measured by the temperature sensors 24 (measured temperatures), i.e. the temperatures of the permanent magnet groups 16a, 16b, are obtained by the controller.

It should be noted here that locations and the number of the temperature sensors 24 are discretional. Also, the temperature sensors 24 may be provided by any known temperature sensor which utilizes a thermocouple, resistance thermometer bulb, thermistor, etc.

Returning to FIG. 1 and FIG. 2, the pole piece 18a includes a disc-like base plate disposed on the opposed surface of the permanent magnet group 16a. The base plate is made of iron for example. The base plate has a main surface formed with a silica steel sheet to prevent generation of eddy current. The silica steel sheet is made of a plurality of block-like layers, and is fixed on the base plate. Further, the base plate has a circumferential edge region formed with an annular projection 26 of iron for example, in order to increase magnetic intensity as well as to improve magnetic field uniformity. In an inner recess on the pole pieces 18a formed by the annular projection 26, an unillustrated gradient coil is disposed. The pole piece 18b is the same as the pole piece 18a.

The plate yokes 12a, 12b are magnetically connected with each other by a support yoke 28 which connects rear end portions of the plate yokes 12a, 12b. The plate yokes 12a, 12b are connected with the support yoke 28 substantially at 90 degrees so as to make a generally U-shaped structure in a side view (See FIG. 2). In addition, the plate yoke 12a has its lower surface (the surface away from the opposed surface) provided with four legs 30.

The magnetic field generator 10 must be able to generate, in its magnetic field space F between the pair of pole pieces 18a, 18b (See FIG. 2), a magnetic field with uniformity accuracy within $1 \times 10^{-4}$ (within 100 PPM) in a range of 0.02 T through 3.0 T. Magnetic characteristics of the permanent magnet groups 16a, 16b change as the temperature of the permanent magnet groups 16a, 16b changes with the room temperature (ambient temperature) in the room where the magnetic field generator 10 is placed. In order to reduce the temperature change of the permanent magnet groups 16a, 16b, a heat insulation member 32 is provided (See FIG. 1). The heat insulation member 32 covers the pair of plate yokes 12a, 12b provided with the magnetic poles 14a, 14b respectively, the support yoke 28 and the four legs 30.

The heat insulation member 32 is made, for example, of an inorganic fiber heat insulation material such as glass wool, or a foamed plastic heat insulation material such as foamed polystyrene and foamed urethane. In order to reduce temperature change more effectively in the permanent magnet groups 16a, 16b, the heat insulation member 32 may be made of a vacuum insulation material which has a smaller thermal conductivity than any of the above heat insulation material used alone. Obviously, an envelope provided by the heat insulation member 32 will reduce temperature change not only of the permanent magnet groups 16a, 16b but also of each element in the magnetic field generator 10.

In order to maintain the permanent magnet groups 16a, 16b at a constant temperature even when the ambient temperature changes, the magnetic field generator 10 further includes tubular heaters 34 incorporated (buried) in the plate yokes 12a, 12b. The tubular heaters 34 which serve as heating means are placed in insertion holes provided in the side surfaces of the plate yokes 12a, 12b. When placing the tubular heaters 34 in the respective insertion holes provided in the plate yokes 12a, 12b, spaces around the heaters are completely filled with heat resistant filler for example, for maximum heat conduction.

The tubular heater 34 can be built with a metal pipe of aluminum or stainless steel for example, a heating element placed therein, and insulation material such as MgO (magnesium oxide) filled in the metal pipe. The tubular heater 34 generates heat from electric power supplied via lead wires from an unillustrated temperature adjuster operated by the controller. Operating time and the amount of heat generation of the tubular heaters 34 are controlled based on a result of comparison between measured temperatures obtained from the temperature sensors 24 and a predetermined target temperature, through adjustment by the controller on the amount of power supply from the temperature adjuster. Specifically, the controller gives the temperature adjuster an instruction to start power supply to the tubular heaters 34 or an instruction to increase power supply to the tubular heaters 34, in response to decrease in the measured temperatures, so as to raise the measured temperatures to the target temperature. Heat generated by the tubular heaters 34 is conducted via the plate yokes 12a, 12b to each of the permanent magnets 20 of the permanent magnet groups 16a, 16b and to each of the heat conducting members 22.

The term "target temperature" is a target value of temperature to be measured by the temperature sensor 24, i.e. a temperature at which the permanent magnet groups 16a, 16b are to be maintained. Heat generated by the tubular heaters 34 is conducted not only to the permanent magnet groups 16a, 16b but also to each element of the magnetic field generator 10, obviously.

According to the magnetic field generator 10 as the above, heat which is conducted from the tubular heaters 34 via the plate yokes 12a, 12b to the permanent magnet groups 16a, 16b is conducted uniformly and quickly through the heat conducting members 22 which have a greater thermal conductivity than the permanent magnets 20, to adjacent permanent magnets 20 in the permanent magnet groups 16a, 16b. Therefore, it is possible to maintain the permanent magnet groups 16a, 16b at a constant temperature easily and uniformly, and to generate a uniform magnetic field of a desired intensity stably in the magnetic field space F.

Further, since heat is easily conducted to each of the permanent magnets 20 in the permanent magnet groups 16a, 16b, it is possible to reduce electric power to be supplied to the tubular heaters 34 and to reduce running cost.

The heat conducting members 22 should preferably be nonmagnetic members in order not to deteriorate uniformity and stability of the magnetic field intensity in the magnetic field space F. The material for the heat conducting members 22 is not limited to aluminum which was mentioned earlier, but the material should preferably have a thermal conductivity not lower than 150 W/m·K. An example of alternative materials to aluminum usable for the heat conducting members 22 is copper. As another example, the heat conducting member 22 may be made of a highly thermal conductive carbon fiber which has a thermal conductivity of 350 W/m·K approx, i.e. higher than aluminum and copper, and is capable of achieving more efficient heat conduction to each of the permanent magnets 20.

The thickness of the heat conducting member 22 is preferably not greater than 10 mm although there is no specific limitation. When the thickness of the heat conducting member 22 is not greater than 10 mm, the distance between the permanent magnets 20 is not excessively large, and the magnetic field intensity in the magnetic field space F is not decreased very much. Uniformity in the magnetic field intensity is not decreased very much, either.

Further, instead of or in addition to the tubular heaters 34, any heaters may be used in any place or in any number. For example, the tubular heaters 34 may be buried in the support yoke 28, or as shown in FIG. 4(a) and FIG. 4(b), surface heaters 35 may be provided on side surfaces of the permanent magnet groups 16a, 16b. As shown in FIG. 4(a), the surface heaters 35 should preferably make contact with each heat conducting member 22. This makes possible to conduct heat more quickly to each of the permanent magnets 20 and thus to the permanent magnet groups 16a, 16b.

Figure 5:
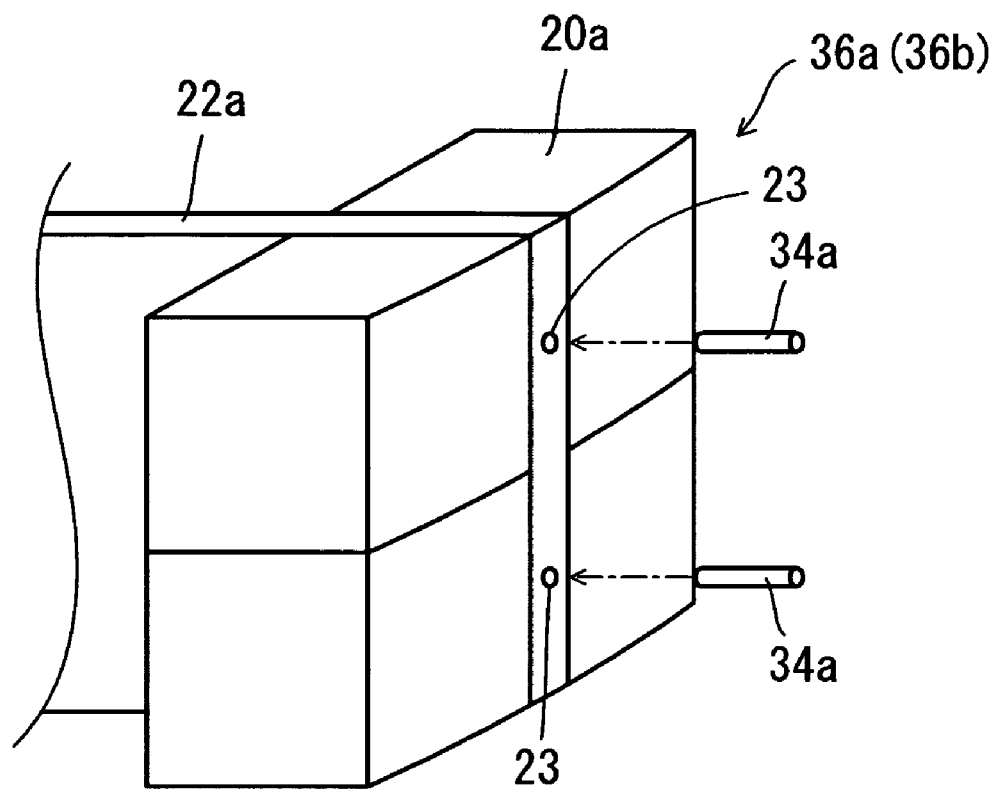
FIG. 5 A schematic perspective view of a primary portion of a permanent magnet group which includes heat conducting members in which tubular heaters are buried.

Another variation is shown in FIG. 5, where permanent magnet groups 36a, 36b are formed of permanent magnets 20a and heat conducting members 22a including an end provided with two insertion holes 23. In each insertion hole 23 there is provided a tubular heater 34a without any space remaining inside the hole. Burying the tubular heaters 34a in the heat conducting members 22a as described enables to deliver heat which is generated by the tubular heaters 34a efficiently to the permanent magnet groups 36a, 36 without allowing the heat to diffuse to the outside as compared to the use of surface heater 35. Additional insertion holes may be made on the end of the heat conducting members 22a, and tubular temperature sensors may be disposed in these insertion holes. It should be noted here that FIG. 5 show part of the permanent magnet groups 36a, 36b.

Generally, the outer diameter of tubular heaters is 5 mm approx. at the smallest, so it becomes difficult to bury the tubular heaters 34a if the heat conducting member is thin. To avoid this, as shown in FIG. 6(a), permanent magnet groups 38a, 38b may be formed of the permanent magnets 20 and heat conducting members 22b which have end portions that follow the side surface of the permanent magnets 20. In this case, tubular heaters 34a are placed in respective insertion holes 23a provided in the end portions of the heat conducting members 22b. Likewise, as shown in FIG. 6(b), permanent magnet groups 40a, 40b may be formed of heat conducting members 22c which have thickened end portions, and permanent magnets 20b have a cutout to be fitted by the end portion of the heat conducting member 22c. In this case, the tubular heaters 34a are placed in insertion holes 23b provided in the thickened end portions of the heat conducting members 22c. It should be noted here that FIG. 6(a) and FIG. 6(b) show part of the permanent magnet groups 38a, 38b, 40a, 40b.

Further, the disposition mode of heat conducting members is not limited to the one used in the above-described permanent magnet groups 16a, 16b. FIG. 7 through FIG. 9 show other disposition mode examples of the heat conducting members in the permanent magnet group.

In FIG. 7(a) and FIG. 7(b), permanent magnet groups 42a, 42b are provided, in addition to heat conducting members 22, with disc-like heat conducting members 22d covering all end surfaces (upper surfaces and lower surfaces) of permanent magnets 20 and of heat conducting members 22. With this arrangement, heat is conducted to each of the permanent magnets 20 and heat conducting members 22 via the heat conducting members 22d which make contact with the opposed surfaces of the plate yokes 12a, 12b, allowing the heat to move further to the heat conducting members 22d disposed on the opposed-surface side of the permanent magnet groups 42a, 42b. Therefore, it is possible to deliver heat to each permanent magnet 20 more uniformly and more quickly than in the case where only one type of heat conducting member 22 is used.

Figure 10:
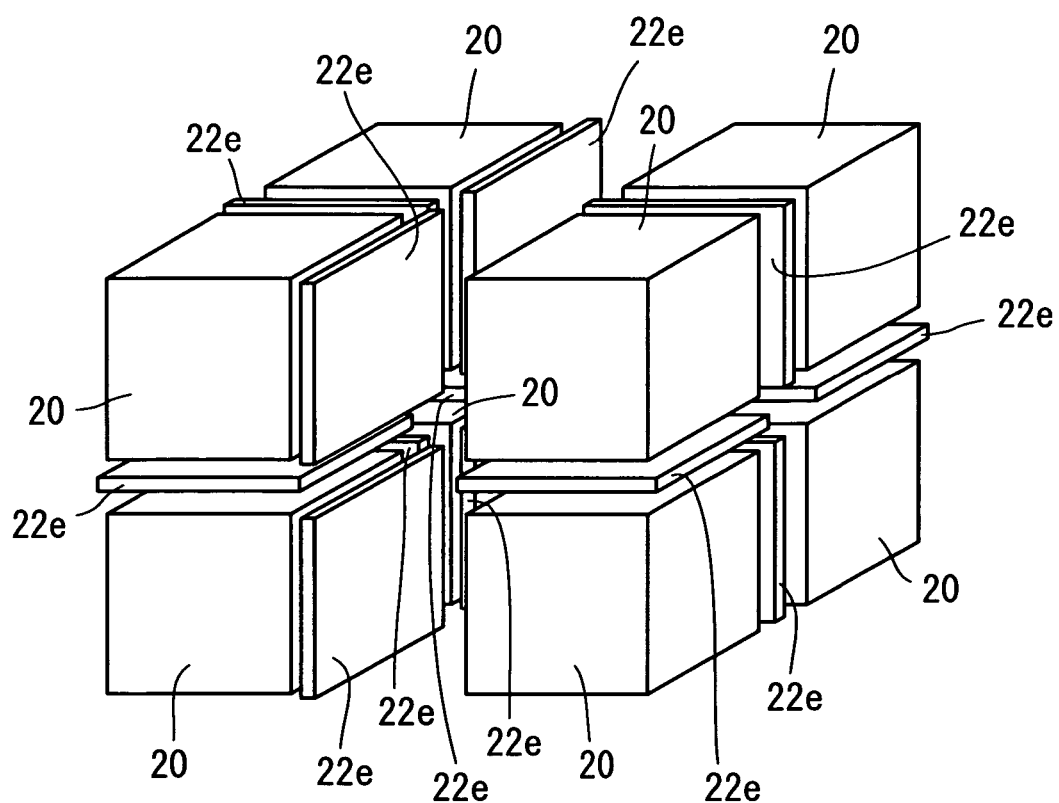
FIG. 10 A perspective view of permanent magnets and heat conducting members which constitute the permanent magnet group in FIG. 8.

FIG. 8(a) and FIG. 8(b) show permanent magnet groups 44a, 44b. As understood also from FIG. 10, a heat conducting member 22e is disposed between those permanent magnets 20 which are mutually adjacent in a top-bottom direction, a left-right direction or an up-down direction. As in an end view, the heat conducting members 22e make a grid-like disposition pattern extending in the top-bottom and the left-right directions. As understood from FIG. 8(a) and FIG. 8(b), each heat conducting member 22e has its end making contact with another. According to the permanent magnet groups 44a, 44b as described, the heat conducting members 22e which is provided between all mutually adjacent permanent magnets 20 enables to deliver heat more uniformly and more quickly to each of the permanent magnets 20.

FIG. 9(a) and FIG. 9(b) show permanent magnet groups 46a, 46b. A heat conducting member 22f is disposed between selected permanent magnets 20 of those which are mutually adjacent in a top-bottom direction or in a left-right direction as in an end view. These heat conducting members 22f are disposed in a cross-like pattern as in an end view. Disposing the heat conducting members 22f in a cross-like pattern in an end view enables to deliver heat uniformly and quickly to center regions of the permanent magnet groups 46a, 46b which have major influence on the uniformity and stability of the magnetic field intensity in the magnetic field space F.

Figure 12:
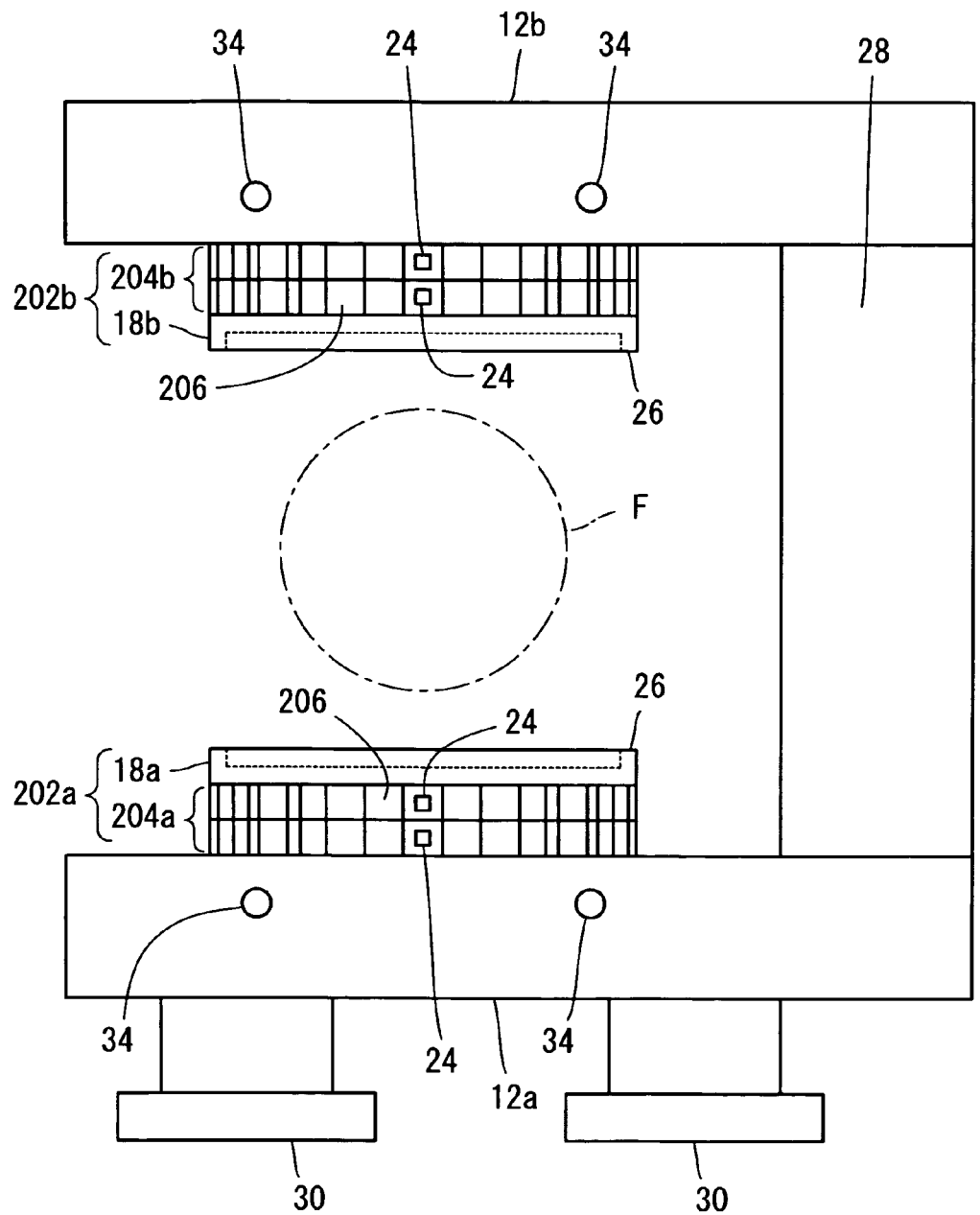
FIG. 12 A schematic side view of a magnetic field generator used in the experiment.

Next, reference will be made to FIG. 11 to describe an experiment example in which magnetic field generators 10 and 200 (See FIG. 12) are used, and measurements were made to the temperature of the permanent magnet groups and the magnetic field intensity while decreasing the ambient temperature.

The magnetic field generators 10 and 200 differ from each other only in that the heat conducting members are not provided between mutually adjacent permanent magnets 206 in permanent magnet groups 204a, 204b which constitute a pair of magnetic poles 202a, 202b in the magnetic field generator 200.

As shown in FIG. 11(a), the ambient temperature was decreased from 25° C. to 20° C. in the experiment, and measurements were made for the temperature of the permanent magnet group 16a in the magnetic field generator 10, and the temperature of the permanent magnet group 204a in the magnetic field generator 200. Further, magnetic field intensity was measured at a plurality of points in the magnetic field space F of the magnetic field generator 10 and at a plurality of points in the magnetic field space F of the magnetic field generator 200. In the experiment, the target temperature was set to 30° C. for each of the magnetic field generators 10 and 200.

FIG. 11 (b) shows temperature change in the permanent magnet groups 16a, 204a. A1 shows a time course observation of the measured temperature detected by the temperature sensor 24 which is provided on a permanent magnet 20 in the lower tier of the permanent magnet group 16a in FIG. 2. B1 shows a time course observation of the measured temperature detected by the temperature sensor 24 which is provided on a permanent magnet 20 in the upper tier of the permanent magnet group 16a in FIG. 2. Likewise, A2 shows a time course observation of the measured temperature detected by the temperature sensor 24 which is provided on a permanent magnet 206 in the lower tier of the permanent magnet group 204a in FIG. 12, whereas B2 shows a time course observation of the measured temperature detected by the temperature sensor 24 which is provided on a permanent magnet 206 in the upper tier of the permanent magnet group 204a in FIG. 12.

Comparison between A1, B1 and A2, B2 reveals: All measured temperature showed decrease as the ambient temperature decreased. However, the temperature decrease was smaller in A1, B1 and the temperature came back to the target temperature more quickly than in A2, B2. Difference in temperature decrease, and difference in the length of time necessary to come back to the target temperature were particularly large between B1 and B2.

This indicates that in the magnetic field generator 10, each heat conducting member 22 was able to deliver heat quickly from the plate yoke 12a to each permanent magnet 20, achieving quicker follow up than in the magnetic field generator 200, when the amount of heat from the tubular heaters 34 was increased. Particularly in the magnetic field generator 200, heat was not delivered as quickly to permanent magnets 206 in the upper tier which did not have contact with the plate yoke 12a, of the permanent magnet group 204a. On the contrary, in the magnetic field generator 10, heat was delivered quickly by the heat conducting members 22 to the permanent magnets 20 in the upper tier of the permanent magnet group 16a.

In A2, B2, the measured temperature approached the target temperature with time, but staggered up and down (indicated by Arrows X1, X2) around the target temperature before the temperature stabilized at the target temperature, and it took a long time before the temperature stabilized at the target temperature. This is a result of poor heat delivery to the permanent magnet group 204a, which lead to a time lag between increase in the amount of heat generated by tubular heaters 34 and temperature increase in the permanent magnet group 204a. As a result, the permanent magnet group 204a was supplied with a more amount of heat than necessary to come back to the target temperature. Such a phenomenon did not take place in A1, B1.

It should be noted here that the same temperature change pattern as in FIG. 11(b) should be observed in the permanent magnet group 16b and the permanent magnet group 204b, obviously.

Next, FIG. 11(c) shows a time course observation on a rate of change in an average magnetic field intensity. C1 represents a time course observation of a rate of change in an average magnetic field intensity in the magnetic field space F of the magnetic field generator 10, whereas C2 represents a time course observation of a rate of change in an average magnetic field intensity in the magnetic field space F of the magnetic field generator 200. The term "average magnetic field intensity" means an average of magnetic field intensity measurements at a plurality of points in the magnetic field space F.

Comparison between C1 and C2 reveals: A maximum value of the rate of change in the average magnetic field intensity was 300 PPM in C1, whereas in C2, a maximum value of the rate of change in the average magnetic field intensity was 500 PPM. In C2, it took time for the permanent magnet groups 204a, 204b of the magnetic field generator 200 to stabilize at the target temperature [See also areas indicated by Arrows X1, X2 in FIG. 11(*b*)]. Because of this, the rate of change in the average magnetic field intensity staggered up and down (indicated by Arrow X3) around 0 PPM before it stabilized at 0 PPM, and it took a long time before stabilizing at 0 PPM. Such a phenomenon did not take place in C1.

Thus, it is understood that in the magnetic field generator 10, temperature change is small in the permanent magnet groups 16a, 16b and it is possible to come back to the target temperature in a short time; therefore, it is possible to generate a magnetic field of a desired intensity more stably in the magnetic field space F than the magnetic field generator 200.

Figure 13:
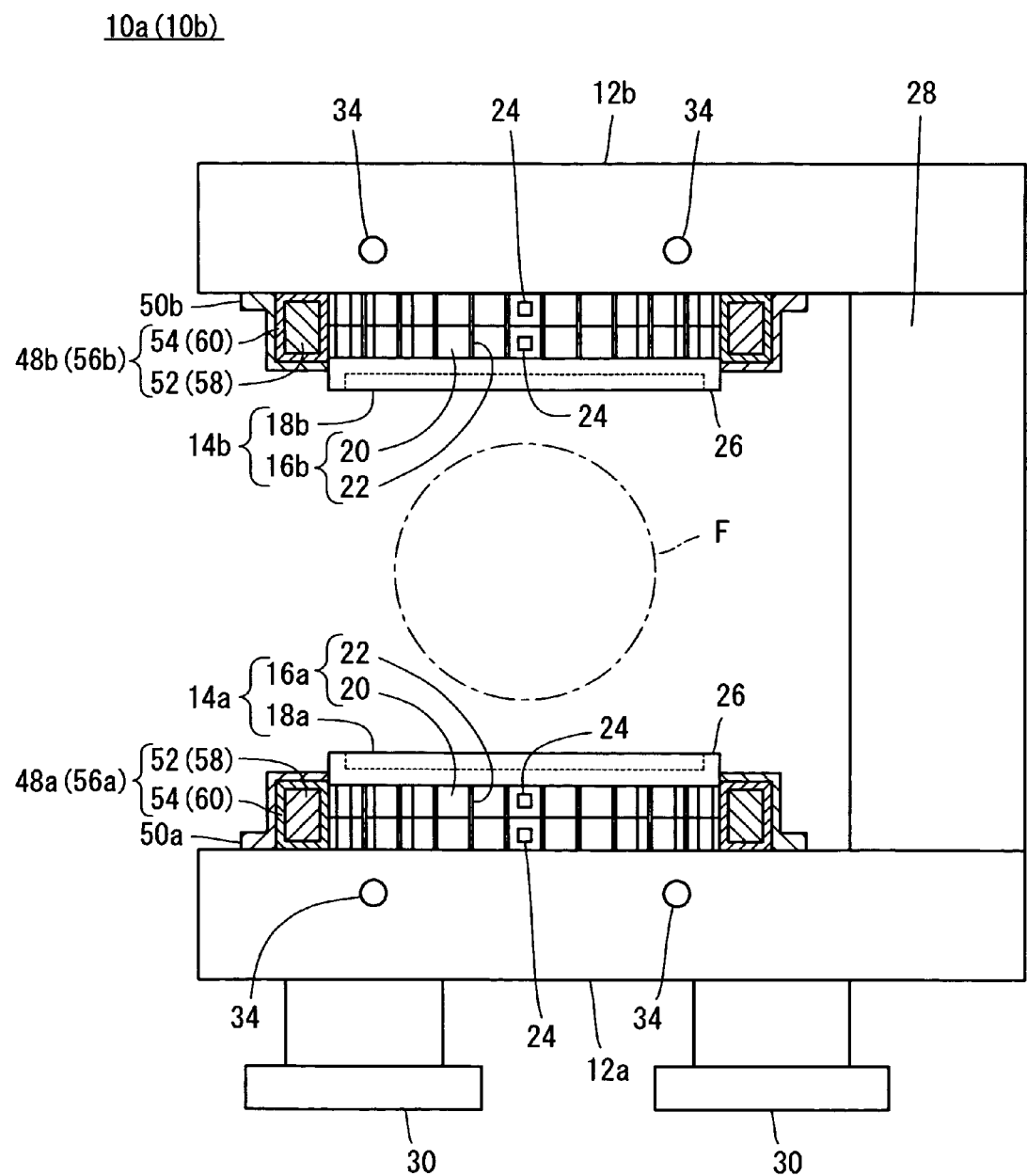
FIG. 13 A schematic side view of another embodiment of the present invention.

Next, description will cover a magnetic field generator 10a as another embodiment of the present invention, with reference to FIG. 13.

The magnetic field generator 10a is the magnetic field generator 10 which is provided with vacuum insulation materials 48a, 48b covering the permanent magnet groups 16a, 16b respectively, and covers 50a, 50b covering the vacuum insulation materials 48a, 48b respectively. All the other aspects are the same with the magnetic field generator 10 and description will not be repeated for the same parts.

The vacuum insulation material 48a is formed annularly, to have an inner diameter essentially the same as the outer diameter of the permanent magnet group 16a, and is disposed on the opposed surface of the plate yoke 12a to cover the side surface of the permanent magnet group 16a. The vacuum insulation material 48b is essentially the same as the vacuum insulation material 48a, and is disposed in the same manner as the vacuum insulation material 48a, on the opposed surface of the plate yoke 12b to cover the side surface of the permanent magnet group 16b.

The cover 50a is fixed on the opposed surface of the plate yoke 12a, and covers the outer circumference of the vacuum insulation material 48a, thereby limiting movements of the vacuum insulation material 48a which makes contact with the side surface of the permanent magnet group 16a. Likewise, the cover 50b is fixed on the opposed surface of the plate yoke 12b so as to limit movements of the vacuum insulation material 48b.

Each of the vacuum insulation materials 48a, 48b includes porous core material 52 made of glass wool as an example of inorganic fiber heat insulation material, and a package 54 made of a laminated aluminum film for holding the core material 52. Inside of the package 54 is vacuum, and the vacuum insulation materials 48a, 48b are provided as vacuum packs of the core material 52 in the package 54. The vacuum insulation materials 48a, 48b as described have a thermal conductivity of 0.01 W/m·K approx. Obviously, a higher level of vacuum in the package 54 will provide a smaller thermal conductivity.

According to the magnetic field generator 10a as described, the vacuum insulation materials 48a, 48b cover the permanent magnet groups 16a, 16b respectively, thereby preventing heat from diffusing from the permanent magnet groups 16a, 16b to the outside, to reduce temperature change of the permanent magnet groups 16a, 16b due to ambient temperature change. Therefore, it is possible to maintain the permanent magnet groups 16a, 16b at a constant temperature more stably.

Further, since heat does not diffuse easily from the permanent magnet groups 16a, 16b to the outside and therefore the temperature of the permanent magnet groups 16a, 16b does not decrease easily, it becomes possible to reduce electric power to be supplied to the tubular heaters 34 and to reduce running cost.

The vacuum insulation materials 48a, 48b may be provided by a plurality of arcuate members.

The material for the core material 52 is not limited to glass wool; any foamed plastic heat insulation material such as foamed polystyrene and foamed urethane or any other material may be used. Likewise, the material for the package 54 is not limited to the laminated aluminum film; plastic film, etc. may be used to form the package 54.

Next, description will cover a magnetic field generator 10b which is also shown in FIG. 13 as is the magnetic field generator 10a. The magnetic field generator 10b differs from the magnetic field generator 10a in that it uses heat storage members 56a, 56b in place of the vacuum insulation materials 48a, 48b. All the other aspects are the same with the magnetic field generator 10a and description will not be repeated for the same parts.

Each of the heat storage members 56a, 56b includes a heat storage material 58 and a package 60 which is formed of a synthetic resin such as polypropylene for holding the heat storage material 58. The heat storage material 58 is preferably provided by an inorganic hydrated salt which has a high heat storage capacity and is able to hold the heat stably. Without any specific limitation to the kind of inorganic hydrated salt to be used as the heat storage material 58, the inorganic hydrated salt should preferably be fire retardant. Examples include calcium chloride hydrates, sodium sulfate hydrates, and sodium acetate hydrates. Other examples than the inorganic hydrated salts usable as the heat storage material 58 are organic compounds such as paraffin. Regardless of the selection, the heat storage material 58 should preferably have a heat storage capacity not smaller than 100 J/g and be fire retardant.

According to the magnetic field generator 10b as described, the heat storage material 58 in each of the heat storage members 56a, 56b keeps the heat of the permanent magnet groups 16a, 16b. When the temperature of the permanent magnet groups 16a, 16b decreases, heat held in the heat storage material 58 is conducted to the permanent magnet groups 16a, 16b. Therefore, it is possible to maintain the permanent magnet groups 16a, 16b at a constant temperature more stably.

Further, when the temperature of the permanent magnet groups 16a, 16b decreases, heat is conducted from the heat storage material 58 to the permanent magnet groups 16a, 16b, so it is possible to reduce electric power to be supplied to the tubular heaters 34 and to reduce running cost.

Figure 14:
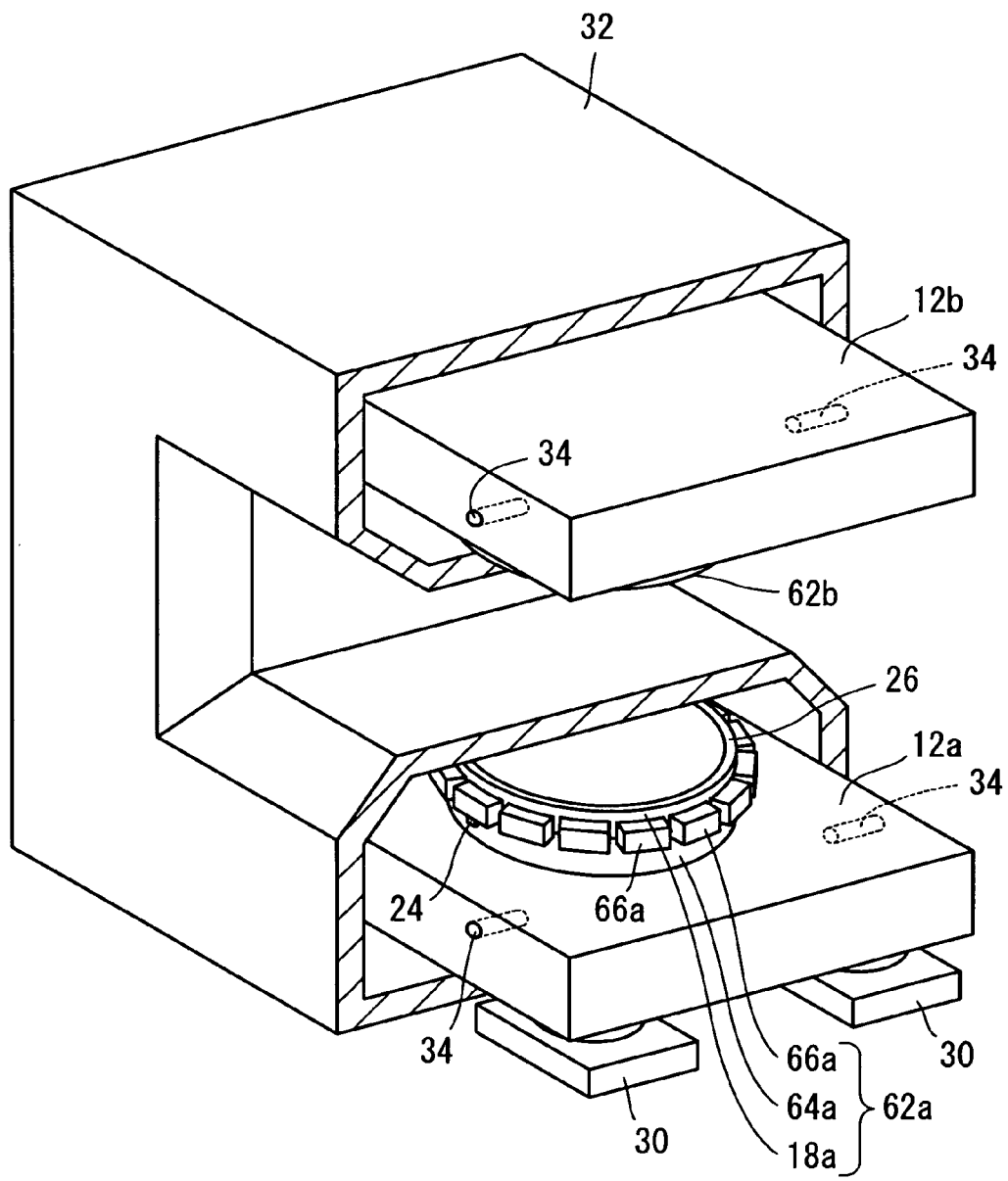
FIG. 14 Schematic perspective view of another embodiment of the present invention.

Next, reference will be made to FIG. 14 and FIG. 15, to describe a magnetic field generator 10c as another embodiment of the present invention.

The magnetic field generator 10c is the magnetic field generator 10 in which the pair of magnetic poles 14a, 14b are replaced by a pair of magnetic poles 62a, 62b. All the other aspects are the same with the magnetic field generator 10 and description will not be repeated for the same parts.

The magnetic pole 62a includes a permanent magnet group 64a, a pole piece 18a, and a plurality of permanent magnet groups 66a. Likewise, the magnetic pole 62b includes a permanent magnet group 64b, a pole piece 18b and a plurality of permanent magnet groups 66b.

Figure 15:
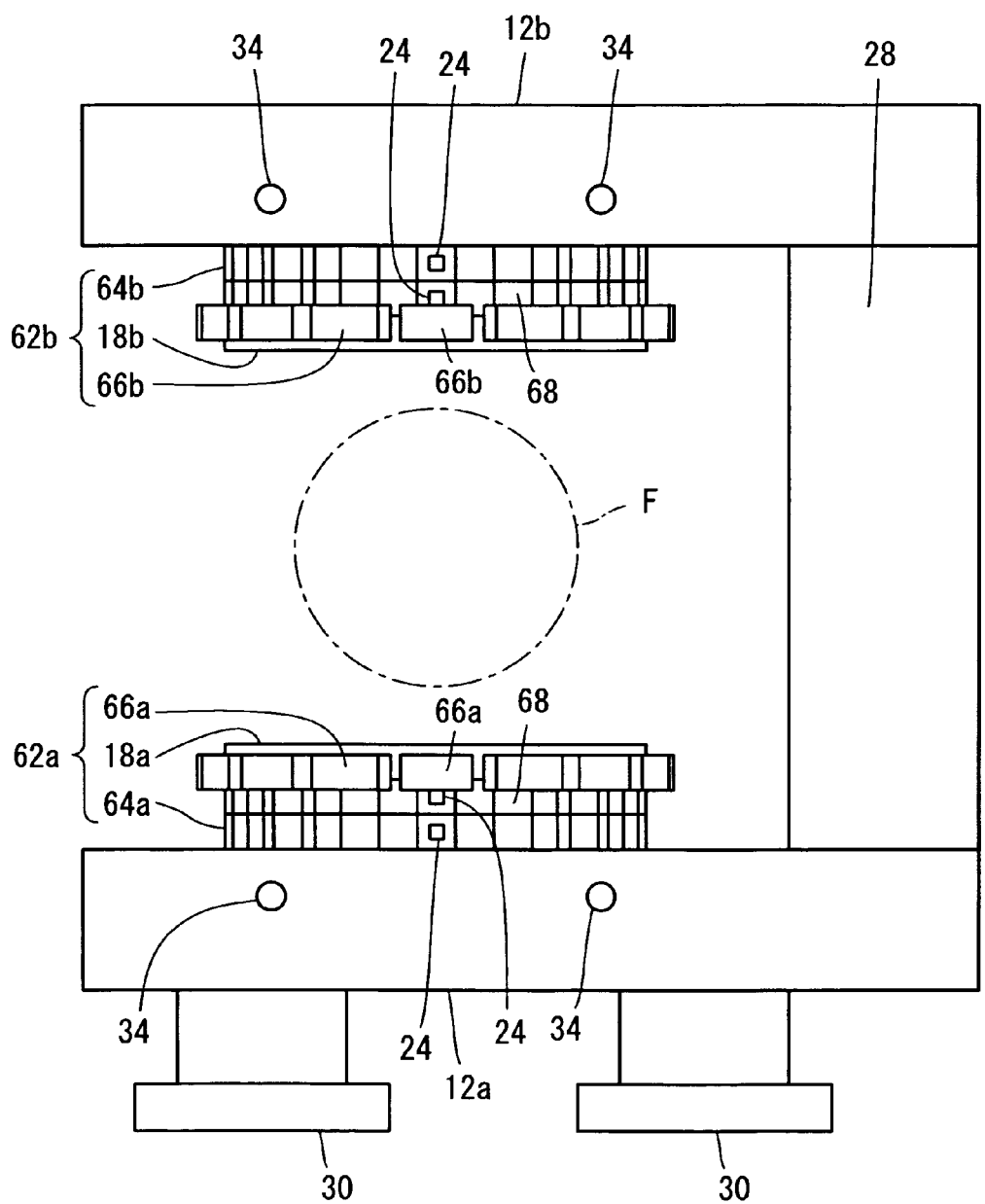
FIG. 15 A schematic side view of the embodiment in FIG. 14.

As shown in FIG. 15, the permanent magnet group 64a is provided by a plurality of permanent magnets 68, and is fixed on the opposed surface of the plate yoke 12a. Likewise, permanent magnet group 64b is provided by a plurality of permanent magnets 68, and is fixed on the opposed surface of the plate yoke 12b. The pole piece 18a is fixed on the opposed surface of the permanent magnet group 64a. Likewise, the pole piece 18b is fixed on the opposed surface of the permanent magnet group 64b. The permanent magnet groups 66a are fixed on an outer side surface of the pole piece 18a to prevent magnetic flux leakage. Likewise, the permanent magnet groups 66b are fixed on an outer side surface of the pole piece 18b to prevent magnetic flux leakage.

It should be noted here that in the present embodiment, the permanent magnet groups 64a, 64b serve as the first permanent magnet groups whereas the permanent magnet groups 66a, 66b serve as the second permanent magnet groups.

As understood from FIG. 16(a) and FIG. 16(b), the permanent magnet group 66a is an integral body of a plurality of permanent magnets 70 and a plurality of heat conducting members 72 formed substantially in a rectangular parallelepiped which has a side surface shaped to fit the outer side surface of the pole piece 18a. As shown in FIG. 16(a) and FIG. 16(b), in the permanent magnet group 66a, the permanent magnets 70 are placed in a front-rear direction [top-bottom direction in FIG. 16(a)] in two rows, as well as in two tiers. Further, in the permanent magnet group 66a, the heat conducting members 72 are disposed between the permanent magnets 70 which are adjacent to each other in a predetermined direction [a left-right direction in FIG. 16(a) and FIG. 16(b)], and extends in a predetermined direction [a top-bottom direction in FIG. 16(a)], making a stripe disposition pattern in an end view. In the permanent magnet group 66a which is fixed on the pole piece 18a, each of the permanent magnets 70 and heat conducting members 72 facing the pole piece 18a makes contact with the pole piece 18a. The permanent magnet group 66b is essentially the same as the permanent magnet group 66a, and is provided on the pole piece 18b in the same manner as is the permanent magnet group 66a.

The permanent magnets 70 used in the permanent magnet groups 66a, 66b are provided by a high coercivity type Nd—Fe—B magnet. The permanent magnets 70 have a thermal conductivity of 9 W/m·K approx. The permanent magnets 70 as described are built with a plurality of unillustrated individual magnets, which are bonded together with adhesive, etc. The heat conducting members 22 are made of aluminum for example, and have a thickness of 0.35 mm. The heat conducting members 72 have a thermal conductivity not lower than 150 W/m·K. It should be noted here that FIG. 16(a) and FIG. 16(b) show the heat conducting member 22 thicker than the actual for easier understanding.

Returning to FIG. 14 and FIG. 15, heat which is generated by the tubular heaters 34 is conducted to the plate yokes 12a, 12b, the permanent magnet group 64a, 64b and then the pole pieces 18a, 18b in this sequence, and is conducted to each of the permanent magnets 70 and heat conducting members 72 in the permanent magnet groups 66a, 66b.

According to the magnetic field generator 10c as the above, heat which is conducted from the tubular heaters 34 via the pole pieces 18a, 18b to the permanent magnet groups 66a, 66b is conducted to mutually adjacent permanent magnets 70 uniformly and quickly through the heat conducting members 72 which have a greater thermal conductivity than the permanent magnets 70. Therefore, even if the permanent magnet groups 66a, 66b are close to the space and are sensitive to ambient temperature, it is possible to maintain a constant temperature easily and uniformly, and to generate a uniform magnetic field of a desired intensity stably in the magnetic field space F.

Further, since heat is easily conducted to each of the permanent magnets 70 in the permanent magnet groups 66a, 66b, it is possible to reduce electric power to be supplied to the tubular heaters 34 and to reduce running cost.

The heat conducting members 72 should preferably be a nonmagnetic member in order not to decrease uniformity and stability of the magnetic field intensity in the magnetic field space F. The material for the heat conducting member 72 is not limited to aluminum which was mentioned earlier, and the heat conducting member 72 may be provided by copper, or a highly thermal conductive carbon fiber, etc.

Further, the disposition mode of the heat conducting members is not limited to the one used in the permanent magnet groups 66a, 66b: For example, the heat conducting members may be placed between all of the permanent magnets 70 which are mutually adjacent in the front-rear direction, the left-right direction or the up-down direction.

Further, the arrangement used for the permanent magnet group 36a, 36b (See FIG. 5) may also be used; specifically, the permanent magnet groups 66a, 66b may use a heat conducting member formed with insertion holes and tubular heaters may be placed in these insertion holes. Burying the tubular heaters in the heat conducting members enables to deliver heat generated by the tubular heaters efficiently to each of the permanent magnets 70 in the permanent magnet groups 66a, 66b without allowing the heat to diffuse to the outside.

Also, as shown in FIG. 17(a) and FIG. 17(b), a plurality of platy heat conducting members 74 may cover the surfaces of permanent magnet groups 66a, 66b. This enables to deliver heat more uniformly and quickly to each of the permanent magnets 70, and therefore to maintain the permanent magnet groups 66a, 66b, which is sensitive to ambient temperature, more stably and uniformly at a constant temperature, and thereby to generate a uniform magnetic field of a desired intensity in the magnetic field space F more stably. Also, heat conducting members provided with insertion holes may be used to cover surfaces of the permanent magnet groups 66a, 66b, with the insertion holes of the heat conducting members provided with tubular heaters.

Figure 18:
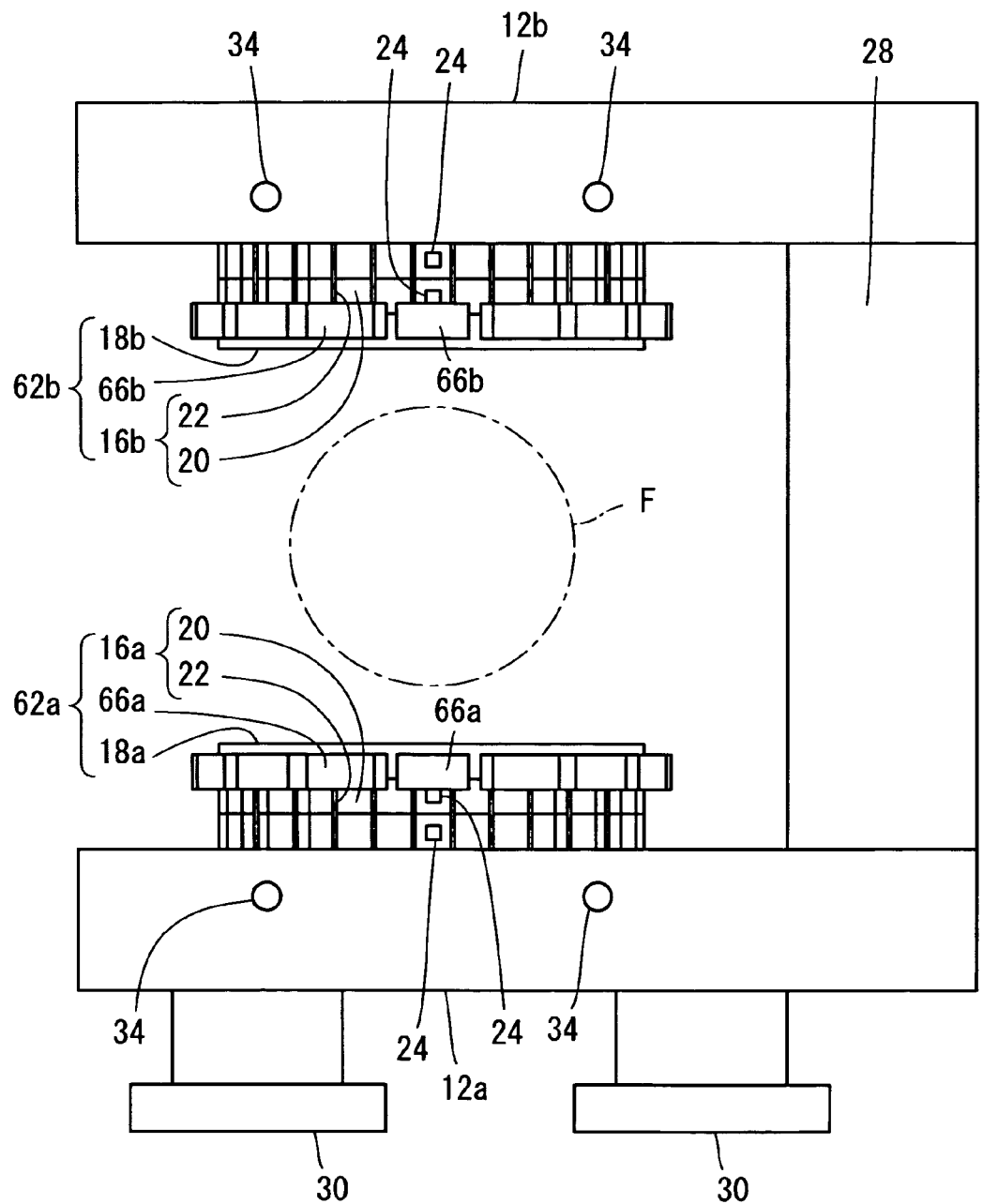
FIG. 18 A schematic side view of another embodiment of the present invention.

Further, the permanent magnet groups 64a, 64b may be replaced by the permanent magnet groups 16a, 16b described earlier, as exemplified in FIG. 18 by a magnetic field generator 10d. This enables to maintain the permanent magnet groups 16a, 16b, 66a and 66b at a constant temperature easily and uniformly and thus to generate a uniform magnetic field of a desired intensity in the magnetic field space F more stably. Also, heat is efficiently conducted through the heat conducting members 22 to the permanent magnet groups 16a, 16b, then to the pole pieces 18a, 18b and to the permanent magnet groups 66a, 66b quickly, so it is possible to reduce electric power to be supplied to the tubular heaters 34 and to reduce running cost.

Next, reference will be made to FIG. 19 to describe a magnetic field generator 10e as another embodiment of the present invention.

The magnetic field generator 10e is the magnetic field generator 10d provided with vacuum insulation materials 76a, 76b which cover the permanent magnet groups 16a, 16b respectively, covers 78a, 78b which cover the vacuum insulation materials 76a, 76b respectively, and vacuum insulation materials 80a, 80b which cover the permanent magnet groups 66a, 66b respectively. All the other aspects are the same with the magnetic field generator 10d and description will not be repeated for the same parts.

The vacuum insulation material 76a is formed annularly, to have an inner diameter essentially the same as the outer diameter of the permanent magnet group 16a, and is disposed on the opposed surface of the plate yoke 12a to cover the side surface of the permanent magnet group 16a. The vacuum insulation material 76b is essentially the same as the vacuum insulation material 76a, and is disposed in the same manner as the vacuum insulation material 76a, on the opposed surface of the plate yoke 12b.

The cover 78a, which is fixed on the opposed surface of the plate yoke 12a, and covers the outer circumference of the vacuum insulation material 76a, thereby limiting movements of the vacuum insulation material 76a which makes contact with the side surface of the permanent magnet group 16a. Likewise, the cover 78b is fixed on the opposed surface of the plate yoke 12b so as to limit movements of the vacuum insulation material 76b.

The vacuum insulation material 80a is formed to have essentially a U-shaped section, and is disposed to cover the outer surfaces of the permanent magnet groups 66a. The vacuum insulation material 80b is essentially the same as the vacuum insulation material 80a, and is disposed in the same manner as the vacuum insulation material 80a, to cover the outer faces of the permanent magnet groups 66b.

Figure 20:
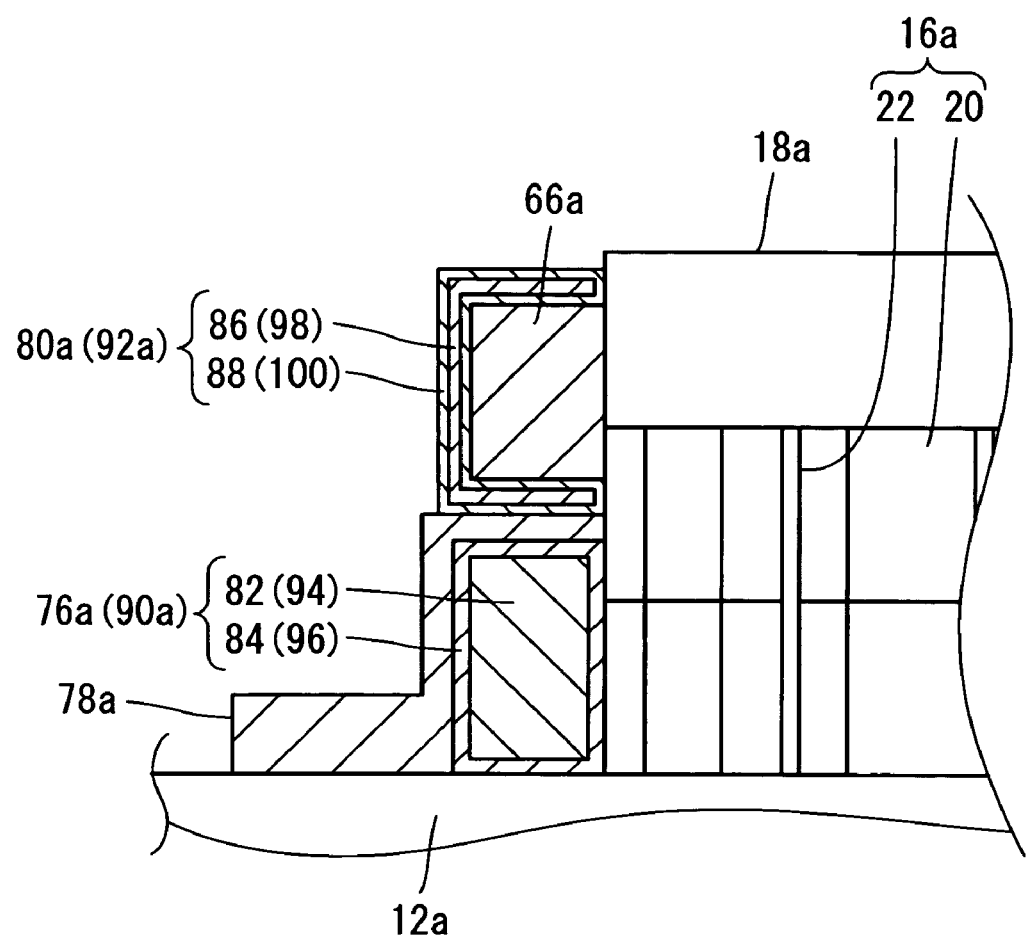
FIG. 20 A schematic sectional view of a vacuum insulation material and a heat storage member.

As shown in FIG. 20, the vacuum insulation material 76a includes a core material 82 and a package 84 which holds the core material 82, and is provided as a vacuum pack of the core material 82 in the package 84. The vacuum insulation material 76b is the same. The vacuum insulation material 80a includes a core material 86 and a package 88 which holds the core material 86, and is provided as a vacuum pack of the core material 86 in the package 88. The vacuum insulation material 80b is the same. The vacuum insulation materials 76a, 76b, 80a and 80b each have a thermal conductivity of 0.01 W/m·K approx. The core materials 82, 86 are made of the same material as used in the core material 52 for the vacuum insulation materials 48a, 48b described earlier whereas the packages 84, 88 are made of the same material as used in the package 54 for the vacuum insulation materials 48a, 48b described earlier.

According to the magnetic field generator 10e as described, the vacuum insulation materials 76a, 76b, 80a and 80b cover the permanent magnet groups 16a, 16b, 66a and 66b respectively, thereby prevent heat from diffusing from the permanent magnet groups 16a, 16b, 66a and 66b to the outside, reduce temperature change of the permanent magnet groups 16a, 16b, 66a and 66b due to ambient temperature change. Therefore, it is possible to maintain the permanent magnet groups 16a, 16b, 66a and 66b at a constant temperature more stably.

Further, heat diffusion from the permanent magnet groups 16a, 16b, 66a and 66b to the outside is decreased and temperature decrease in the permanent magnet groups 16a, 16b, 66a and 66b is less; therefore it is possible to reduce electric power to be supplied to the tubular heaters 34 and to reduce running cost.

It should be noted here that the magnetic field generator 10e may be provided with the vacuum insulation materials 76a, 76b alone or with the vacuum insulation materials 80a, 80b, alone.

Figure 19:
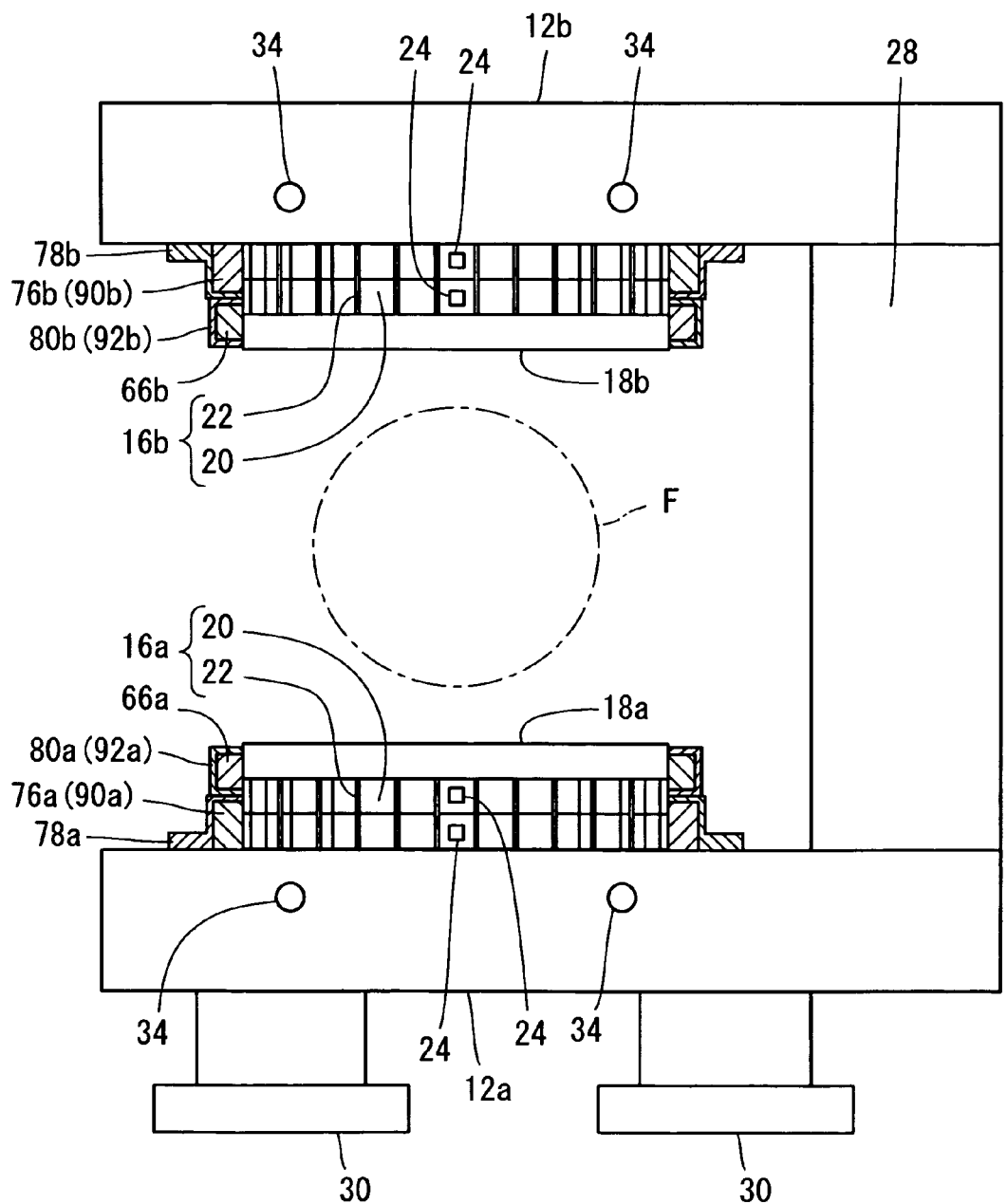
FIG. 19 A schematic side view of another embodiment of the present invention.

Next, description will cover a magnetic field generator 10f which is also shown in FIG. 19 as is the magnetic field generator 10e. The magnetic field generator 10f uses heat storage members 90a, 90b, 92a and 92b in place of the vacuum insulation materials 76a, 76b, 80a and 80b.

As shown in FIG. 20 the heat storage members 90a includes a heat storage material 94 and a package 96 which holds the heat storage material 94. The heat storage member 90b is the same. The heat storage member 92a includes a heat storage material 98 and a package 100 which holds the heat storage material 98. The heat storage member 92b is the same. The heat storage materials 94, 98 are made of the same material as used in the heat storage material 58 for the heat storage members 56a, 56b described earlier whereas the packages 96, 100 are made of the same material as used in the package 60 for the heat storage members 56a, 56b described earlier.

According to the magnetic field generator 10f as described, the heat storage material 94 in each of the heat storage members 90a, 90b keeps the heat of the permanent magnet groups 16a, 16b, and the heat storage material 98 in each of the heat storage members 92a, 92b keeps the heat of the permanent magnet groups 66a, 66b. When the temperature of the permanent magnet groups 16a, 16b decreases, heat held in the heat storage material 94 is conducted to the permanent magnet groups 16a, 16b. When the temperature of the permanent magnet groups 66a, 66b decreases, heat held in the heat storage material 98 is conducted to the permanent magnet groups 66a, 66b. Therefore, it is possible to maintain the permanent magnet groups 16a, 16b, 66a and 66b at a constant temperature more stably.

Further, when the temperature of the permanent magnet groups 16a, 16b decreases, heat is conducted from the heat storage material 94 to the permanent magnet groups 16a, 16b, and when the temperature of the permanent magnet groups 66a, 66b decreases, heat is conducted from the heat storage material 98 to the permanent magnet groups 66a, 66b. Thus, it is possible to reduce electric power to be supplied to the tubular heaters 34 and to reduce running cost.

It should be noted here that in the magnetic field generator 10e, the vacuum insulation materials 80a, 80b may be replaced by the heat storage members 92a, 92b. Likewise, in the magnetic field generator 10f, the heat storage members 92a, 92b may be replaced by the vacuum insulation materials 80a, 80b.

Figure 21:
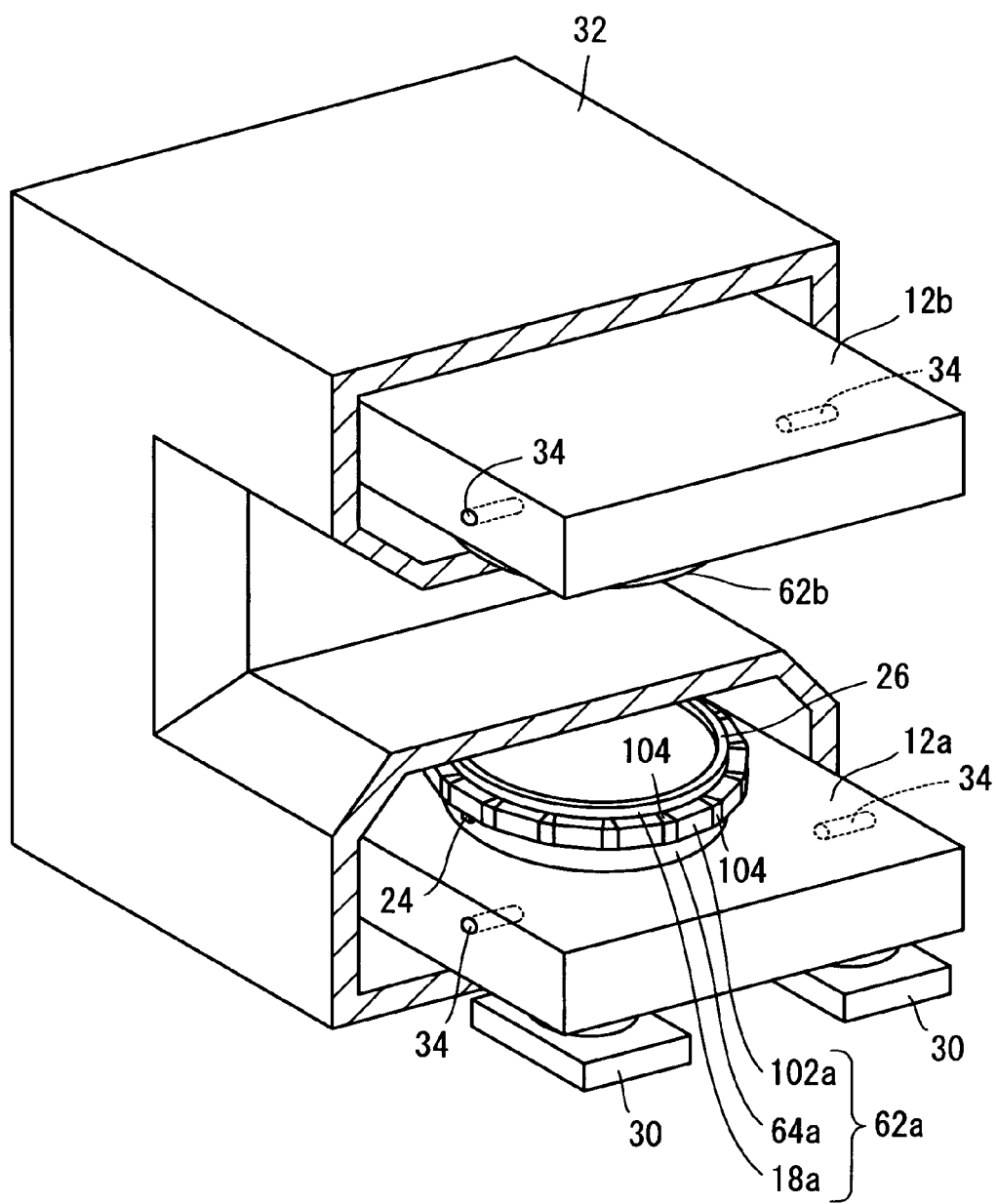
FIG. 21 A schematic perspective view of another embodiment of the present invention.
Figure 22:
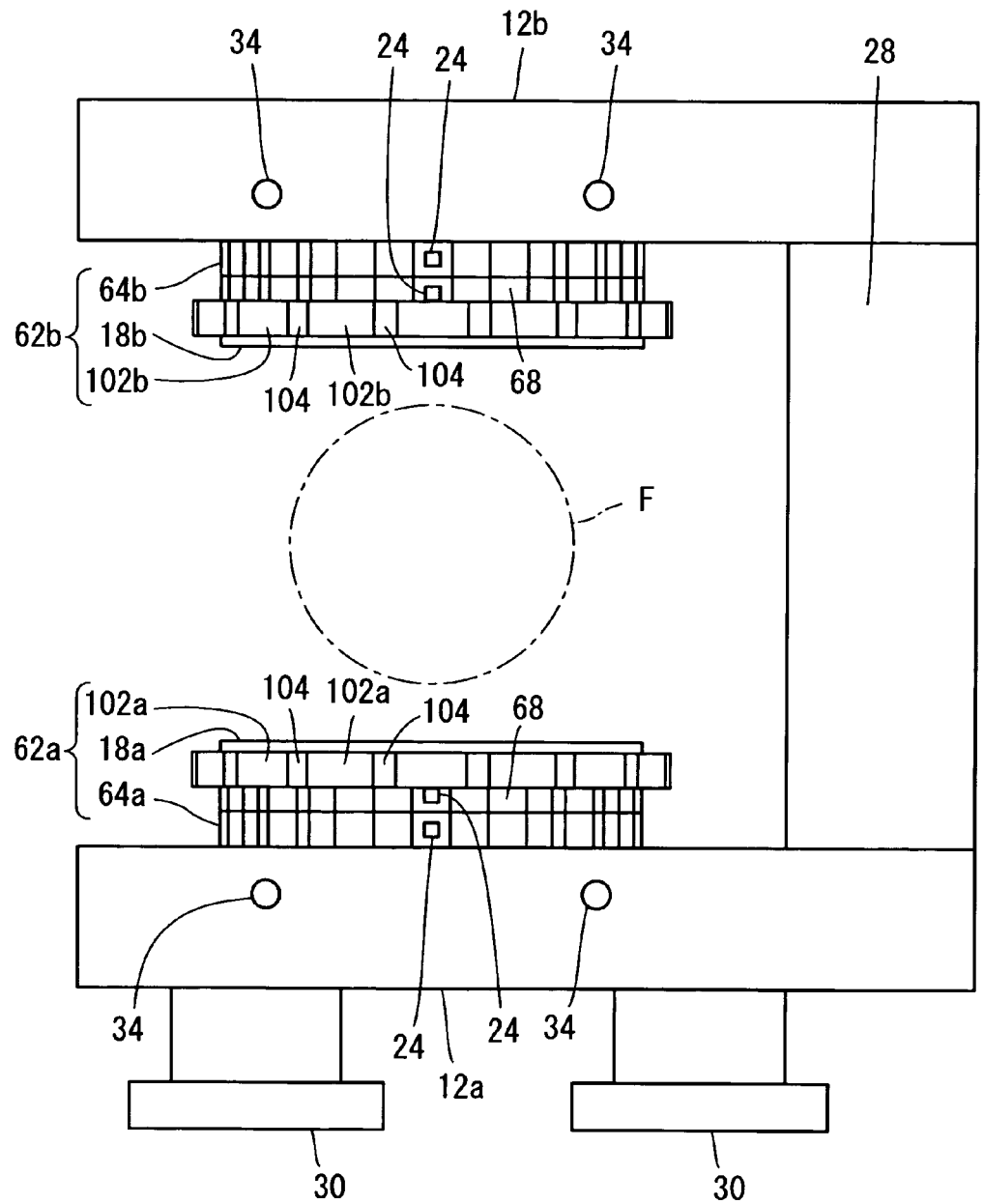
FIG. 22 A schematic side view of the embodiment in FIG. 21.

Next, reference will be made to FIG. 21 and FIG. 22, to describe a magnetic field generator 10g as another embodiment of the present invention.

The magnetic field generator 10g is the magnetic field generator 10c described earlier, in which the permanent magnet groups 66a, 66b are replaced by permanent magnet groups 102a, 102b, with a heat conducting member 104 placed between mutually adjacent permanent magnet groups 102a as well as between mutually adjacent permanent magnet groups 102b. All the other aspects are the same with the magnetic field generator 10c and description will not be repeated for the same parts.

As understood from FIG. 23(a) and FIG. 23(b), the permanent magnet groups 102a are fixed on an outer side surface of the pole piece 18a, and each is made of a plurality of unillustrated permanent magnets formed substantially in a rectangular parallelepiped which has a side surface shaped to fit the outer side surface of the pole piece 18a. Further, mutually adjacent permanent magnet groups 102a sandwich the heat conducting member 104. The permanent magnet groups 102a and the heat conducting members 104 are provided as a single-piece structure, with each making contact with the pole piece 18a. The permanent magnet groups 102b and the heat conducting members 104 which are provided on the outer side surface of the pole piece 18b have the same structure.

It should be noted here that in the present embodiment, the permanent magnet groups 64a, 64b serves as the first permanent magnet groups whereas the permanent magnet group 102a, 102b serves as the second permanent magnet groups.

The permanent magnet groups 102a, 102b are made of the same kind of permanent magnets as the permanent magnets 70 used in the permanent magnet groups 66a, 66b. Also, the heat conducting members 104 are made of the same kind of material as used for the heat conducting members 72 described earlier.

Returning to FIG. 21 and FIG. 22, heat which is generated by the tubular heaters 34 is conducted to the plate yokes 12a, 12b, the permanent magnet groups 64a, 64b and then the pole pieces 18a, 18b in this sequence, and is conducted to each of the permanent magnet groups 102a, 102b and heat conducting members 104.

According to the magnetic field generator 10g as the above, heat of the tubular heater 34 which is conducted from the pole pieces 18a, 18b is conducted uniformly and quickly through the heat conducting members 104, to each of the permanent magnet groups 102a, 102b. Therefore, even if the permanent magnet groups 102a, 102b are sensitive to ambient temperature, it is possible to maintain the permanent magnet groups 102a, 102b at a constant temperature easily and uniformly, to reduce temperature difference in each of the permanent magnet groups 102a, 102b, and to generate a uniform magnetic field of a desired intensity stably in the magnetic field space F.

Further, since heat is easily conducted to each of the permanent magnet groups 102a, 102b, it is possible to reduce electric power to be supplied to the tubular heaters 34 and to reduce running cost.

Further, the arrangement only requires placement of a heat conducting member 104 at each gap between mutually adjacent permanent magnet groups 102a, and between mutually adjacent permanent magnet groups 102b. This enables to reduce the number of parts in the magnetic field generator, to reduce the number of manufacturing steps, and to reduce manufacturing cost as compared to the permanent magnet groups 66a, 66b described above in which a heat conducting member 72 is disposed between mutually adjacent permanent magnets 70.

Figure 24:
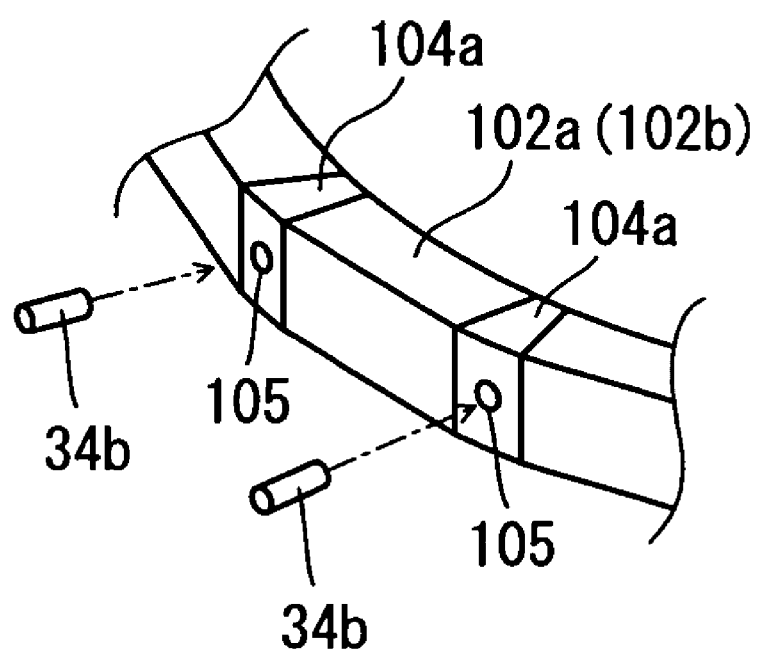
FIG. 24 A schematic perspective view of heat conducting members as an example, disposed between permanent magnet groups provided on an outer side surface of the pole piece, with tubular heater buried in each heat conducting member.

It should be noted here that, as shown in FIG. 24, the heat conducting members 104 may be replaced by heat conducting members 104a which are formed with insertion holes 105, and tubular heaters 34b may be placed in these insertion holes 105 in place of the tubular heaters 34 or in addition to the tubular heaters 34. Burying the tubular heaters 34b in the heat conducting members 104a as described enables to deliver heat efficiently to each of the permanent magnet groups 102a, 102b without allowing the heat which is generated by the tubular heaters 34b to diffuse to the outside.

Further, as shown in FIG. 25(a) and FIG. 25(b), both end surfaces (upper surface and lower surface) in each of the permanent magnet groups 102a, 102b and in each of the heat conducting members 104 may be covered by a platy, annular heat conducting members 106. This enables to deliver heat to each of the permanent magnet groups 102a, 102b more uniformly and quickly. Therefore, it is possible to maintain the permanent magnet group 102a, 102b which are sensitive to ambient temperature, more stably and uniformly at a constant temperature and to generate a uniform magnetic field of a desired intensity more stably in the magnetic field space F.

Further, the permanent magnet groups 64a, 64b may be replaced by the permanent magnet groups 16a, 16b described earlier. This enables to maintain the permanent magnet groups 16a, 16b, 102a and 102b easily and uniformly at a constant temperature, and to generate a uniform magnetic field of a desired intensity more stably in the magnetic field space F.

Further, vacuum insulation materials or heat storage members which have an essentially U-shaped section and are shaped annularly may be disposed to cover each of the permanent magnet group 102a, 102b and heat conducting members 104. This enables to maintain each of the permanent magnet groups 102a, 102b at a constant temperature more stably.

Next, the present invention is also applicable to a box type magnetic field generator 300 as shown in FIG. 26(a). Hereinafter, reference will be made to FIG. 26(a) through FIG. 26(c) to describe the magnetic field generator 300 as another embodiment of the present invention.

The magnetic field generator 300 includes a pair of rectangular parallelepiped permanent magnet groups 302a, 302b [See FIG. 26(b)]. As shown in FIG. 26(c), the permanent magnet group 302a is surrounded by (has each of its side surfaces provided with) rectangular parallelepiped permanent magnet groups 304a, 306a, 308a and 310a. The permanent magnet group 302a is magnetically connected with the permanent magnet groups 304a, 306a, 308a and 310a.

Figure 27:
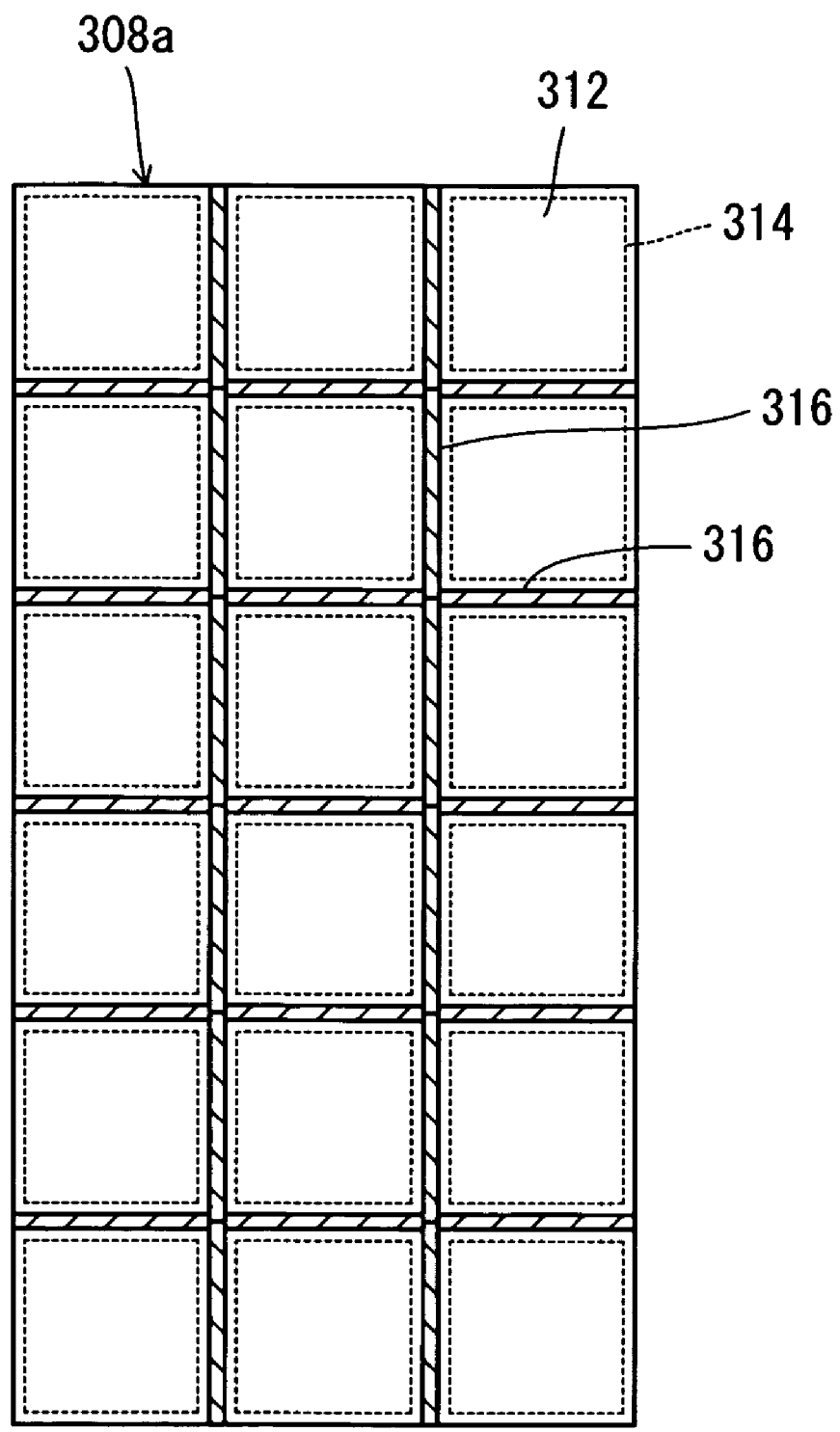
FIG. 27 A schematic front view of the permanent magnet group in FIG. 26.
Figure 29:
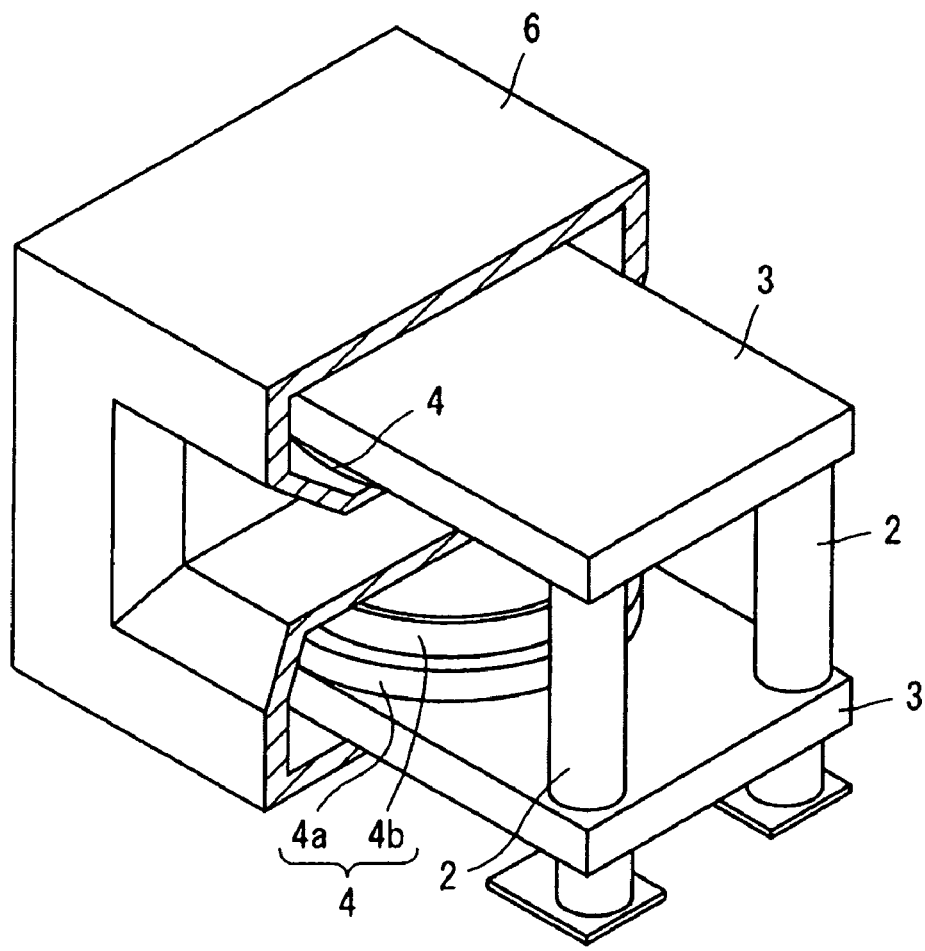

As shown in FIG. 27, each of the permanent magnet groups used in the magnetic field generator 300 is an integral body formed substantially in a cubic shape, of a plurality of permanent magnets 314 each coated with a coating material 312, and heat conducting members 316 disposed between mutually adjacent permanent magnets 314. The coating material 312 is made of aluminum, nickel, copper, etc, formed by surface treatment (coating) by known method such as vapor deposition and metal plating, to coat the permanent magnet 314 entirely. The coating material 312 has a thickness of 30 μm approx. as it coats the permanent magnet 314. By giving the coating material 312 a thickness of 30 μm approx. as described, heat is conducted efficiently via the coating material 312 to the permanent magnet 314. The material for the coating material 312 is not limited to aluminum, nickel, copper or the like, but the material should preferably have a thermal conductivity of 150 W/m·K. It should be noted here that FIG. 27 shows a side surface (front surface) of the permanent magnet group 308a.

Returning to FIG. 26(c), with the permanent magnet group 302a in between, the permanent magnet groups 304a, 306a are disposed to face with each other. On each of the opposed surfaces, a heat conducting member 318 is provided. Similarly, with the permanent magnet groups 302a, 304a and 306a in between, the permanent magnet groups 308a, 310a are disposed to face with each other, and on each of the opposed surfaces, a heat conducting member 320 is provided. In each of the permanent magnet groups 308a, 310a, a heat conducting member 320 is also provided on a surface which faces away from the opposed surface. The heat conducting members 320 provided on the opposed surfaces of the permanent magnet groups 308a, 310a make contact with ends of the heat conducting members 318 which are provided on the opposed surfaces of the permanent magnet groups 304a, 306a.

Surrounds of the permanent magnet group 302b are essentially the same as of the permanent magnet group 302a, and should be understood simply by replacing the alphabetical code "a" with "b" in FIG. 26(c), without any more description.

As shown in FIG. 26(a) and FIG. 26(b), a permanent magnet group 322a is provided between the permanent magnet groups 308a, 308b whereas a permanent magnet group 322b is provided between the permanent magnet group 310a, 310b, providing a space between the permanent magnet groups 302a and 302b.

With the space in between, the permanent magnet group 322a, 322b are disposed to face with each other. On each of their opposed surfaces and surfaces away from the opposed surfaces, a heat conducting member 324 is provided. Each heat conducting member 324 has its end contacted with an end of the heat conducting member 320.

A heat conducting member 326 is provided between the permanent magnet groups 308a, 322a. The heat conducting member 326 which is provided between the permanent magnet groups 308a, 322a is flush with the heat conducting members 320 which are faced to each other with the permanent magnet group 308a in between. Likewise, heat conducting members 326 are provided between the permanent magnet groups 308b and 322a, between the permanent magnet groups 310a and 322b, and between the permanent magnet groups 310b and 322b respectively.

The permanent magnet group 302a has a lower surface provided with a ferromagnetic member 328a. Likewise, the permanent magnet group 302b has an upper surface provided with a ferromagnetic member 328b. The "ferromagnetic member" is a member which has a saturation magnetization not smaller than 1.0 T. The ferromagnetic members 328a, 328b are provided for example, by electromagnetic soft iron, JIS:S15C, or permendur (an Iron-Cobalt alloy).

The ferromagnetic member 328a has its opposed surface provided with a pole piece 330a. Likewise, the ferromagnetic member 328b has its opposed surface provided with a pole piece 330b. In the magnetic field generator 300, a magnetic field space is formed between the pole pieces 330a, 330b inside the space. The ferromagnetic members 328a, 328b have their respective opposed surfaces provided with heat conducting members 332 which cover outer side surfaces of the pole pieces 330a, 330b.

The heat conducting member 332 which covers the outer side surface of the pole piece 330a extends on the lower surfaces of the permanent magnet groups 304a, 306a and of the ferromagnetic member 328a. Likewise, the heat conducting member 332 which covers the outer side surface of the pole piece 330b extends on the upper surfaces of the permanent magnet groups 304b, 306b and of the ferromagnetic member 328b.

The heat conducting members 316, 318, 320, 324, 326, 332 are made of the same material as used for the heat conducting member 22 described earlier.

As shown in FIG. 26(a), a tubular heater 334 is buried in the heat conducting member 332. Also, in the heat conducting member 332, a tubular temperature sensor 336 is buried near the tubular heater 334. The tubular heater 334 is placed inside an insertion hole formed in the heat conducting member 332, without leaving any space in the insertion hole. Likewise, the temperature sensor 336 is placed inside an insertion hole formed in the heat conducting member 332, without leaving any space in the insertion hole. Heat generated by the tubular heater 334 is conducted quickly to each element of the magnetic field generator 300 via the heat conducting member 332.

Burying the tubular heaters 334 and the temperature sensors 336 into the heat conducting members 332 and disposing the temperature sensors 336 near the tubular heaters 334 as described enable to sense the heat from the tubular heaters 334 quickly by the temperature sensors 336, and therefore to prevent the tubular heaters 334 from generating an unnecessary amount of heat. Since the tubular heaters 334 are close to each of the permanent magnet groups in the magnetic field generator 300, thermal demagnetization can occur in the permanent magnets 314 which constitute the permanent magnet groups if the amount of heat generated by the tubular heaters 334 becomes excessively large. However, quick sensing of heat by the temperature sensors 336 enables to prevent this.

The permanent magnet group 302a has an upper surface provided with a plate yoke 338a whereas the permanent magnet group 302b has a lower surface provided with a plate yoke 338b. The plate yokes 338a, 338b are connected with each other by yokes 340a, 340b each formed like a letter n having two legs. The two legs on each of the yokes 340a, 340b make contact with heat conducting members 320 respectively. The yokes 340a, 340b have their side surfaces provided with surface heaters 342. Heat generated by the surface heaters 342 is conducted quickly via the yokes 340a, 340b to the heat conducting members 320, and then via the heat conducting members 320 to each of the elements in the magnetic field generator 300.

It should be noted here that each element of the magnetic field generator 300 may be covered by a heat insulation member, made of a vacuum insulation material for example, which has an opening corresponding to the space.

According to the magnetic field generator 300 as described, a coat provided by the coating material 312 on each of the permanent magnets 314 enables more uniform and quicker conduction of heat from the tubular heaters 334 and surface heaters 342 to each of the permanent magnets 314 than in the case where the heat conducting members 316 are placed simply between mutually adjacent permanent magnets 314. Therefore, it is possible to maintain each permanent magnet group uniformly at a constant temperature and more stably, and to generate a uniform magnetic field of a desired intensity stably in the magnetic field generation space which is formed between the permanent magnet groups 302a, 302b.

Further, since heat is conducted easily to each of the permanent magnets 314 in each of the permanent magnet groups, it is possible to reduce electric power to be supplied to the tubular heaters 334 and the surface heater 342 and to reduce running cost.

It should be noted here that in the magnetic field generator 300, description was made for a case in which all of the permanent magnets 314 are coated by the coating material 312: Alternatively, coating by the coating material 312 may be provided only to selected permanent magnets 314 which are considered to have relatively large influence to the magnetic field intensity and uniformity of the magnetic field intensity. Also, coating by the coating material 312 may be provided partially on the surface of the permanent magnet 314.

Also, coating by the coating material 312 may be provided to each of the permanent magnets 20 in the permanent magnet groups 16a, 16b described earlier. Likewise, coating by the coating material 312 may be provided to each of the permanent magnets 70 in the permanent magnet groups 66a, 66b described earlier.

The present invention is applicable to any magnetic field generators. For example, the present invention is applicable to magnetic field generators disclosed in JP-A 2004-41715.

The present invention being thus far described and illustrated in detail, it is obvious that these description and drawings only represent examples of the present invention, and should not be interpreted as limiting the invention. The spirit and scope of the present invention is only limited by words used in the accompanied claims.

The invention claimed is:

1. A magnetic field generator comprising:
a pair of magnetic poles each including a first permanent magnet group having a plurality of permanent magnets, and a pole piece provided on an end surface of the first permanent magnet group, the pole pieces being faced to each other with a space in between;

heating means for supplying heat to at least the pair of magnetic poles; and a heat conducting member made of a nonmagnetic member and provided between mutually adjacent permanent magnets at least in part of the first permanent magnet group, the heat conducting member making contact with each surface of the adjacent permanent magnets.

2. The magnetic field generator according to claim 1, wherein each of the magnetic poles further includes a second permanent magnetic group having a plurality of permanent magnets and provided on an outer side surface of the pole piece, the magnetic field generator further comprising a heat conducting member provided between mutually adjacent permanent magnets at least in part of the second permanent magnet group.

3. A magnetic field generator comprising:

a pair of magnetic poles each including a first permanent magnet group having a plurality of permanent magnets, a pole piece provided in an end surface of the first permanent magnet group, and a plurality of second permanent magnet groups each including a plurality of permanent magnets and provided on an outer side surface of the pole piece, the pole pieces being faced to each other with a space in between;

heating means for supplying heat to at least the pair of magnetic poles; and a heat conducting member made of a nonmagnetic member and provided between mutually adjacent second permanent magnet groups at least in part of the second permanent magnet groups, the heat conducting member making contact with each surface of the adjacent permanent magnet groups.

4. The magnetic field generator according to claim 1, 2 or 3, further comprising a coating material formed on at least part of the permanent magnets and having a thermal conductivity not lower than 150 W/m·K.

5. The magnetic field generator according to claim 1, 2 or 3, further comprising a temperature sensor disposed near the heating means.

6. The magnetic field generator according to claim 1, further comprising a heat insulation material covering the first permanent magnet group.

7. The magnetic field generator according to claim 6, wherein the heat insulation material is provided by a vacuum insulation material.

8. The magnetic field generator according to claim 1, further comprising a heat storage member covering the first permanent magnet group.

9. The magnetic field generator according to claim 8, wherein the heat storage member includes a heat storage material provided by an inorganic hydrated salt.

10. A magnetic field generator comprising:

a pair of magnetic poles each including a first permanent magnet group having a plurality of permanent magnets, a pole piece provided on an end surface of the first permanent magnet group, and a second permanent magnet group including a plurality of permanent magnets and provided on an outer side surface of the pole piece, the pole pieces being faced to each other with a space in between;

heating means for supplying heat to at least the pair of magnetic poles; and a heat conducting member made of a nonmagnetic member and provided between mutually adjacent permanent magnets at least in part of the second permanent magnet group, the heat conducting member making contact with each surface of the adjacent permanent magnets.

11. The magnetic field generator according to claim 2, further comprising a heat conducting member provided on at least part of a surface of the second permanent magnet group.

12. The magnetic field generator according to claim 11, wherein the heating means is buried in the heat conducting member.

13. The magnetic field generator according to claim 10, further comprising a heat insulation material covering the second permanent magnet group.

14. The magnetic field generator according to claim 13, wherein the heat insulation material is provided by a vacuum insulation material.

15. The magnetic field generator according to claim 10, further comprising a heat storage member covering the second permanent magnet group.

16. The magnetic field generator according to claim 15, wherein the heat storage member includes a heat storage material provided by an inorganic hydrated salt.

17. The magnetic field generator according to claim 1, 2 or 3, wherein the heating means is buried in the heat conducting member.

* * * * *

UNITED STATES PATENT AND TRADEMARK OFFICE
CERTIFICATE OF CORRECTION

| | |
|---|---|
| PATENT NO. | : 7,733,090 B2 |
| APPLICATION NO. | : 11/631259 |
| DATED | : June 8, 2010 |
| INVENTOR(S) | : Masaaki Aoki |

It is certified that error appears in the above-identified patent and that said Letters Patent is hereby corrected as shown below:

On the Title page:

Item "(87)" PCT Pub. No.: should read as --Jan. 12, 2006--

Signed and Sealed this

Third Day of August, 2010

David J. Kappos
*Director of the United States Patent and Trademark Office*

UNITED STATES PATENT AND TRADEMARK OFFICE
CERTIFICATE OF CORRECTION

PATENT NO.         : 7,733,090 B2
APPLICATION NO. : 11/631259
DATED              : June 8, 2010
INVENTOR(S)        : Masaaki Aoki It is certified that error appears in the above-identified patent and that said Letters Patent is hereby corrected as shown below:

In Column 22, line 64, Item "(The invention claimed is:)", through Column 24, line 46. The attached claims are the correct allowed claims.

--1. A magnetic field generator comprising:
a pair of magnetic poles each including a first permanent magnet group having a plurality of permanent magnets, and a pole piece provided on an end surface of the first permanent magnet group, the pole pieces being faced to each other with a space in between;
heating means for supplying heat to at least the pair of magnetic poles; and
a heat conducting member made of a nonmagnetic member and provided between mutually adjacent permanent magnets at least in part of the first permanent magnet group, the heat conducting member making contact with each surface of the adjacent permanent magnets.

2. The magnetic field generator according to Claim 1, wherein each of the magnetic poles further includes a second permanent magnetic group having a plurality of permanent magnets and provided on an outer side surface of the pole piece,
the magnetic field generator further comprising a heat conducting member provided between mutually adjacent permanent magnets at least in part of the second permanent magnet group.

3. The magnetic field generator according to Claim 1, further comprising a heat insulation material covering the first permanent magnet group.--

In Column 22, line 64, Item "(The invention claimed is:)", through Column 24, line 46. The attached claims are the correct allowed claims.

--4. The magnetic field generator according to Claim 3, wherein the heat insulation material is provided by a vacuum insulation material.

Signed and Sealed this

Thirtieth Day of November, 2010

David J. Kappos
*Director of the United States Patent and Trademark Office*

5. The magnetic field generator according to Claim 1, further comprising a heat storage member covering the first permanent magnet group.

6. The magnetic field generator according to Claim 5, wherein the heat storage member includes a heat storage material provided by an inorganic hydrated salt.

7. A magnetic field generator comprising:
a pair of magnetic poles each including a first permanent magnet group having a plurality of permanent magnets, a pole piece provided on an end surface of the first permanent magnet group, and a second permanent magnet group including a plurality of permanent magnets and provided on an outer side surface of the pole piece, the pole pieces being faced to each other with a space in between;
heating means for supplying heat to at least the pair of magnetic poles; and
a heat conducting member made of a nonmagnetic member and provided between mutually adjacent permanent magnets at least in part of the second permanent magnet group, the heat conducting member making contact with each surface of the adjacent permanent magnets.--

In Column 22, line 64, Item "(The invention claimed is:)", through Column 24, line 46. The attached claims are the correct allowed claims.

--8. The magnetic field generator according to Claim 7, further comprising a heat insulation material covering the second permanent magnet group.

9. The magnetic field generator according to Claim 8, wherein the heat insulation material is provided by a vacuum insulation material.

10. The magnetic field generator according to Claim 7, further comprising a heat storage member covering the second permanent magnet group.

11. The magnetic field generator according to Claim 10, wherein the heat storage member includes a heat storage material provided by an inorganic hydrated salt.--

In Column 22, line 64, Item "(The invention claimed is:)", through Column 24, line 46. The attached claims are the correct allowed claims.

--12. A magnetic field generator comprising:
a pair of magnetic poles each including a first permanent magnet group having a plurality of permanent magnets, a pole piece provided in an end surface of the first permanent magnet group, and a plurality of second permanent magnet groups each including a plurality of permanent magnets and provided on an outer side surface of the pole piece, the pole pieces being faced to each other with a space in between;
heating means for supplying heat to at least the pair of magnetic poles; and
a heat conducting member made of a nonmagnetic member and provided between mutually adjacent second permanent magnet groups at least in part of the second permanent magnet groups, the heat conducting member making contact with each surface of the adjacent second permanent magnet groups.

13. The magnetic field generator according to Claim 12, further comprising a heat conducting member provided on at least part of a surface of the second permanent magnet group.

14. The magnetic field generator according to Claim 13, wherein the heating means is buried in the heat conducting member.--

In Column 22, line 64, Item "(The invention claimed is:)", through Column 24, line 46. The attached claims are the correct allowed claims.

--15. The magnetic field generator according to Claim 1, 7 or 12, wherein the heating means is buried in the heat conducting member.

16. The magnetic field generator according to Claim 1, 7 or 12, further comprising a coating material formed on at least part of the permanent magnets and having a thermal conductivity not lower than 150W/m · K.

17. The magnetic field generator according to Claim 1, 7 or 12, further comprising a temperature sensor disposed near the heating means.--